United States Patent [19]
Graeve et al.

[11] Patent Number: 5,627,173
[45] Date of Patent: May 6, 1997

[54] PHOSPHONOACETIC ACID DERIVATIVES AND THEIR USE FOR TREATING DEGENERATIVE JOINT DISORDERS

[75] Inventors: Rolf Graeve, Taunustein; Werner Thorwart, Hochheim; Ruth Raiss, Frankfurt; Klaus U. Weithmann, Hofheim; Stefan Müllner, Hochheim, all of Germany

[73] Assignee: Hoechst Aktiengesellschaft, Frankfurt am Main, Germany

[21] Appl. No.: 590,300

[22] Filed: Jan. 23, 1996

[30] Foreign Application Priority Data

Jan. 25, 1995 [DE] Germany ......................... 195 02 209.2

[51] Int. Cl.$^6$ .......................... A61K 31/66; C07F 9/38; C07F 9/40
[52] U.S. Cl. ......................... 514/120; 514/89; 514/90; 514/95; 514/100; 514/105; 514/112; 514/114; 544/157; 546/22; 549/7; 549/220; 556/19
[58] Field of Search .................. 558/82, 167, 179, 558/182; 562/24; 514/105, 112, 120

[56] References Cited

U.S. PATENT DOCUMENTS 5,137,897 8/1992 Thorwart et al. ...................... 514/365

FOREIGN PATENT DOCUMENTS

| 0559079 | 9/1993 | European Pat. Off. . |
| 0601573 | 6/1994 | European Pat. Off. . |
| WO94/19358 | 9/1994 | WIPO . |

OTHER PUBLICATIONS

Cho, Hidetsura et al.; "Novel Caffeic Acid Derivatives: Extremely Potent Inhibitors of 12-Lipoxygenase" Journal of Medicinal Chemistry 34(1991): 1503–1505. 1991.

T. Saeki et al., "Isolation of Cyclic Nucleotide Phosphodiesterase Isozymes From Pig Aorta", Biochemical Pharmacology, 46(5):833–839 (1993).

J. Chenault et al., "Side Reactions in the Phase Transfer Catalysed Wittig–Horner Synthesis. A Convenient Method of Preparation of Hydroxycinnamic Acids", Synthetic Communications, 14(11):1059–1065 (1984).

P. Magnus et al., "Synthesis of the Antileukemic Agent ( )–Steganone Using a Stereoconvergent Biaryl Coupling Reaction", J. Am. Chem. Soc., vol. 107, pp. 4984–4988, 1985.

C. Pollers–Wieers et al., "The Use of Isoquinolinetriones in the Synthesis of Benzo[C]Phenanthridine Alkaloids", Tetrahedron, 37(24–N):4321–4326, 1981.

J. Levine et al., "Intraneuronal Substance P Contributes to the Severity of Experimental Arthritis", Science, 226:547–549 (1984).

D. Burkhardt et al., "Laboratory Evaluation of Glycosaminoglycan Polysulphate Ester for Chondroprotective Activity: A Review", Current Therapeutic Research, 40(6):1034–1053 (1986).

B. Pernow, "Substance P", Pharmacological Reviews, 35(2):85–141 (1983).

K. Kimura et al., "1–4–Di:hydro–pyridine–3–phosphonic acid derivatives", Derwent abstract 84–251757 (1984).

Chem. Ab. 102(15):132271y, "Dihydrohyridyl phosphate derivatives", Nippon Shinyaku Co., Ltd. Jpn., Kokai Tokyo Koho, 41 et seq., 1984.

Bartlett et al., "New 4–hydroxy phenyl–thiazole–2carboxylic acid derivs.—are antiinflammatories, immunomodulators, inhibitors of lipoxygenase, etc. esp. for control of inflammatory rhematic disease", Derwent ab. 008675569 (1991).

Chemical Abstracts, No. 185122e, vol. 114, No. 19, May 13, 1991.

Chemical Abstracts, No. 24234e, vol. 102, No. 3, Jan. 21, 1985.

Chemical Abstracts, No. 55549d, vol. 66, No. 13, Mar. 27, 1967.

*Primary Examiner*—Johann Richter
*Assistant Examiner*—Michael G. Ambrose
*Attorney, Agent, or Firm*—Finnegan, Henderson, Farabow, Garrett & Dunner, L.L.P.

[57] ABSTRACT

Phosphonoacetic acid derivatives and their use for treating degenerative joint disorders Compounds of the formula I

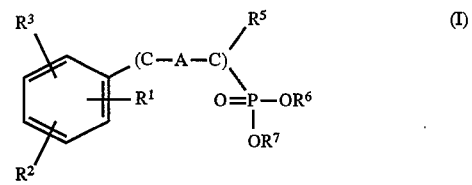

are suitable for producing pharmaceuticals for the treatment and prophylaxis of degenerative joint disorders, of rheumatic disorders accompanied by cartilage breakdown, such as rheumatoid arthritis, joint trauma and chondrolysis as a consequence of prolonged immobilization of the joint, of inflammations, septic shock, disorders with impaired leukocyte adhesion, disorders caused by an elevated concentration of tumor necrosis factor alpha, such as cachexia or Crohn's disease.

32 Claims, No Drawings

PHOSPHONOACETIC ACID DERIVATIVES AND THEIR USE FOR TREATING DEGENERATIVE JOINT DISORDERS

Osteoarthritis is a degenerative joint disorder with inflammatory episodes and progressive cartilage dysfunction which may lead to impairment of function or even complete ankylosis. Although to date the concomitant inflammations and states of pain associated with this disorder can be treated, there are no available pharmaceuticals which have been proven to be able to stop or cure the progressive cartilage breakdown. Examples of known therapeutic agents for osteoarthritis are mixtures of sulfated glucosaminoglycans (Current Therapeutic Research, 40, 6 (1986) 1034) or non-steroidal anti-inflammatory drugs, but these are unable to stop the loss of cartilage. Although the pathogenesis of osteoarthritis and arthritis has not yet been elucidated in detail, it is regarded as certain that the chondrocytes (cartilage cells) are crucially involved in the increased loss of matrix, and that, of the main constituents of this matrix, in particular the proteoglycans (PG) are the first to undergo enzymatic breakdown.

Thus, promising medicaments for the therapy of osteoarthritis are those which, because of their profile of action, stimulate proteoglycan synthesis in chondro cytes and, furthermore, counteract a pathologically increased rate of cartilage breakdown. Moreover, the breakdown of proteoglycans can be reduced either by inhibiting matrix metalloproteinases or else by deactivating reactive oxygen free radicals. Another approach to the therapy of arthritis is the increased concentration of substance P in arthritis. Substance P (SP) is a neuropeptide which is widespread both in the central nervous system and in the peripheral nervous system (Pernow, Pharmacological Reviews 35: 85–141, 1983). The effect and importance of SP in arthritis has been known since 1984 (J. Levine et al., Science, 226: 547 549, 1984). There is evidently a correlation between the SP concentration in the joints and the severity of the arthritis.

It has now been found that the compounds of the formula I according to the invention stimulate proteoglycan synthesis in cartilage, inhibit the pathologically increased enzymatic cartilage breakdown and effectively reduce the cartilage destruction induced by oxygen free radicals. It has furthermore been found that the compounds according to the invention antagonize the effects of substance P.

Phosphonoacetic acid derivatives are described in the following documents: pollers-Wieër, C. et al., Tetrahedron 37: 4321 to 4326, 1981; Magnus, P. et al., J. Am. Chem. Soc. 107: 4984 to 4988, 1985; Chenault, J. and Dupin, J., Synth. Commun. 14: 1059 to 1065, 1984. The vasodilator effect of a phosphonoacetic acid derivative is described in the document Nippon Shinyako Co. Ltd., Jpn. Kokai Tokyo Koho 41 et seq., 1984.

The invention relates to a compound selected from at least one of a compound of the formula (I)

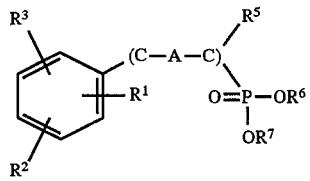

a physiologically tolerated salt thereof, or a stereoisomer thereof where at least two of the radicals $R^1$, $R^2$ and $R^3$ are present and are, independently of one another, 1) OH,
2) $(C_1-C_{12})$-alkoxy,
3) —O—$(C_1-C_{12})$-alkyl-COOH,
4) —O—$(C_1-C_{12})$-alkyl-C(O)—O—$(C_1-C_{12})$-alkyl,
5) $(C_3-C_{12})$-cycloalkoxy,
6) $(C_3-C_6)$-alkenyloxy,
7) $(C_5-C_7)$-cycloalkyl-$(C_1-C_3)$-alkoxy,
8) heteroaryl-$(C_1-C_3)$-alkoxy, where the heteroatoms are N, S and/or O,
9) heterocycloalkyl-$(C_1-C_3)$-alkoxy where the heteroatoms are N, S and/or O, the heterocycloalkyl radical is unsubstituted or substituted once to three times by $(C_1-C_3)$-alkyl, and the heterocycloalkyl group has five or six members,
10) phenyl-$(C_1-C_3)$-alkoxy,
11) benzyloxy substituted once to three times by halomethyl or $(C_1-C_3)$-alkoxy,
12) phenoxy substituted once to three times by $(C_1-C_3)$-alkoxy,
13) two of the radicals $R^1$, $R^2$ or $R^3$ which are substituents on two directly adjacent carbon atoms of the aromatic ring together form a methylenedioxy or ethylenedioxy radical on the aromatic ring,
14) a radical of the formula II, III or IV

where $R^8$ is $(C_1-C_4)$-alkyl, or hydrogen 15) a group of the formula V

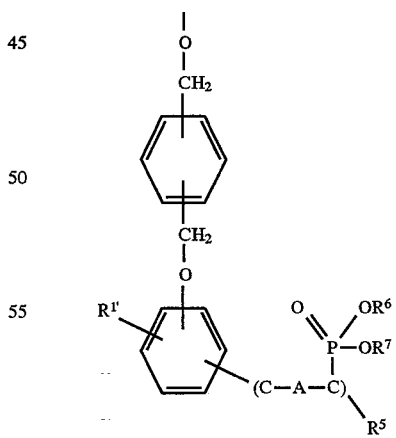

where $R^1$ is defined as for $R^1$ from 1) to 12), and (C-A-C), $R^5$, $R^6$ and $R^7$ are as defined below, or 16) $R^1$ and $R^7$ are a covalent bond and thus form a compound of the formula Ia

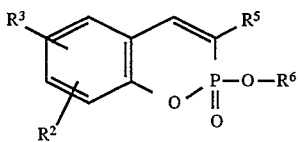
(Ia)

where $R^2$ and $R^3$ are as defined above and $R^5$ and $R^6$ are as defined below, or 17) $R^1$ and $R^5$ are a covalent bond and thus form a compound of the formula Ib

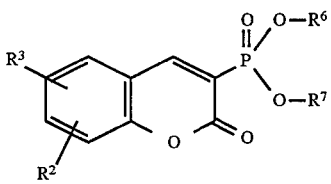
(Ib)

where $R^2$ and $R^3$ are as defined above and $R^6$ and $R^7$ are as defined below, and $R^5$ is 1) CN,
2) $CH_2NHR^9$ where $R^9$ is hydrogen or —C(O)—($C_1$-$C_3$)-alkyl, or
3) a radical of the formula VI

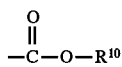
(VI)

where $R^{10}$ is 1) hydrogen,
2) ($C_1$-$C_6$)-alkyl, unsubstituted or substituted once to four times by —COOH, C(O)—O— ($C_1$-$C_3$)-alkyl or 2.3

where

R is hydrogen, ($C_1$-$C_3$)-alkyl or forms, together with the nitrogen atom to which it is bonded, a morpholine ring, or
3) trialkylsilyl, $R^6$ and $R^7$ are, independently of one another, 1) hydrogen or
2) ($C_1$-$C_6$)-alkyl, (C-A-C) is 1) (CH=CH—CH=C),
2) ($CH_2$—$CH_2$—$CH_2$—CH),
3) ($CH_2$—$CH_2$—CH),
4) (—$CH_2$—CH) or
5) (—CH=C)

with the proviso that when the radical $R^5$ is a CN group, not more than one of the radicals $R^1$, $R^2$ or $R^3$ is a hydroxyl radical, or when the radical $R^{10}$ is a hydrogen atom, none of the radicals $R^1$, $R^2$ or $R^3$ is a hydroxyl radical, or when the radical $R^{10}$ is methyl, ethyl or t-butyl, the radicals $R^1$, $R^2$ or $R^3$ are not methoxy, and the compounds

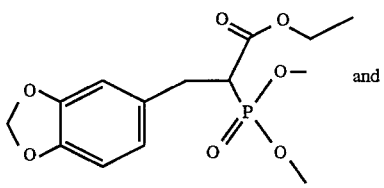
and

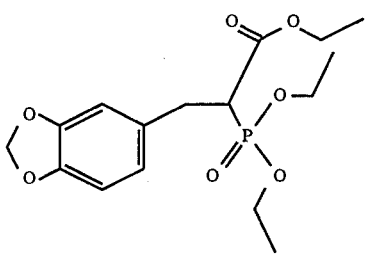

are excepted.

A preferred embodiment of the present invention is a compound of the formula I where at least two of the radicals $R^1$, $R^2$ and $R^3$ are present and are, independently of one another, 1) OH,
2) ($C_1$-$C_6$)-alkoxy,
3) —O—($C_1$-$C_6$)-alkyl-COOH,
4) —O—($C_1$-$C_6$)-alkyl-C(O)—O—($C_1$-$C_6$)-alkyl,
5) ($C_5$-$C_7$)-cycloalkoxy,
6) ($C_3$-$C_6$)-alkenyloxy,
7) ($C_5$-$C_7$)-cycloalkyl-($C_1$-$C_2$)-alkoxy,
9) heterocycloalkyl-($C_1$-$C_2$)-alkoxy where the heteroatoms are N and/or O, the heterocycloalkyl radical is unsubstituted or substituted once to three times by ($C_1$-$C_3$)-alkyl, and the heterocycloalkyl group has five or six members,
10) phenyl-($C_1$-$C_2$)-alkoxy,
11) benzyloxy substituted once to three times by halomethyl or ($C_1$-$C_3$)-alkoxy,
12) phenoxy substituted once to three times by ($C_1$-$C_3$)-alkoxy,
13) two of the radicals $R^1$, $R^2$ or $R^3$ are both a group of the formula (II)

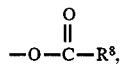
(II)

where $R^8$ is ($C_1$-$C_4$-alkyl, and $R^5$ is

1) CN,
2) $CH_2NHR^9$ where $R^9$ is hydrogen or —C(O)—($C_1$-$C_3$)-alkyl, or
3) a radical of the formula VI

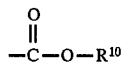
(VI)

where $R^{10}$ is 1) hydrogen,
2) ($C_1$-$C_6$)-alkyl, unsubstituted or substituted once by
   1) —COOH,
   2) —C(O)—($C_1$-$C_3$)-alkyl or

3)

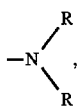

where R is ($C_1$–$C_3$)-alkyl, or 3) trialkylsilyl, $R^6$ and $R^7$ are, independently of one another, hydrogen or ($C_1$–$C_4$)-alkyl, and (C-A-C) is 1) (—$CH_2$—CH) or 2) (—CH═C)

Particularly preferred is a compound of the formula I where $R^1$ is methoxy,
$R^2$ is methoxy or benzyloxy,
$R^3$ is methoxy or benzyloxy, and
$R^4$ is
1) CN,
2) $CH_2NHR^9$ where $R^9$ is hydrogen or —C(O)—($C_1$–$C_2$)-alkyl or
3) a radical of the formula VI, where $R^{10}$ is
    1) hydrogen or
    2) ($C_1$–$C_4$)-alkyl substituted by
       1) —COOH,
       2)

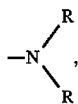

where R is hydrogen atom and/or ($C_1$–$C_3$)-alkyl, $R^6$ and $R^7$ are, independently of one another, hydrogen or ($C_1$–$C_4$)-alkyl, and (C-A-C) is a (—CH═C) radical.

Furthermore, a compound of the formula I where $R^1$ is hydrogen and $R^2$ and $R^3$ are both methoxy, and $R^5$ is a group of the formula VI where $R^{10}$ is hydrogen or isopropyl, $R^6$ and $R^7$ are both ethyl or methyl, and (C-A-C) is a (—$CH_2$—CH) radical, is also preferred.

In addition, a compound of the formula I where $R^1$ is hydrogen and $R^2$ and $R^3$ are both benzyloxy, and $R^5$ is a group of the formula VI where $R^{10}$ is hydrogen or isopropyl, $R^6$ and $R^7$ are methyl or ethyl, and (C-A-C) is a (—CH═C) radical, is very particularly preferred.

The terms alkyl and alkoxy mean radicals whose carbon chains are straight-chain or branched. The cyclic alkyl radicals of the cycloalkyl groups are, in particular, 5-to 7-membered monocycles such as cyclopentyl, cyclohexyl and cycloheptyl. The heteroaryl radicals of the heteroarylalkoxy groups are, in particular, radicals such as pyridyl and thienyl. The heterocycloalkyl radicals of the heterocycloalkylalkoxy groups are, in particular, radicals such as piperidinyl and morpholinyl. Halogen in the radical halomethyl is fluorine, chlorine, bromine or iodine.

The definition "two of the radicals $R^1$, $R^2$ or $R^3$ which are substituents on two directly adjacent carbon atoms of the aromatic ring together form a methylenedioxy or ethylenedioxy radical on the aromatic ring" includes, for example, the 1,3-dioxolene or 1,4-dioxan-2-ene radicals.

The invention furthermore relates to a process for preparing the compound of the formula I, with one embodiment comprising a) reacting a compound of the formula VII

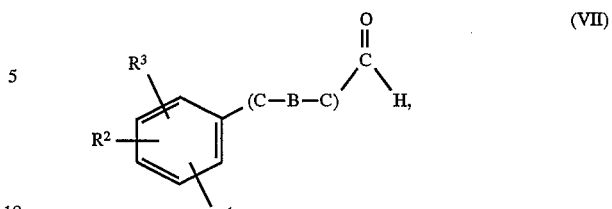

where $R^1$, $R^2$ and $R^3$ are as defined in formula I, and (C-B-C) is a covalent bond, (—CH═CH—), (—$CH_2$—$CH_2$—$CH_2$), (—$CH_2$—$CH_2$) or (—$CH_2$—), with a compound of the formula VIII or with a salt of a compound of the formula VIII

where $R^5$, $R^6$ and $R^7$ are defined as in formula I, in the presence of tetrahydrofuran and titanium tetrachloride or in the presence of tetrahydrofuran and an orthotitanic triester of the formula IX (IX) 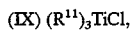($R^{11}$)$_3$TiCl, where $R^{11}$ is O-($C_1$–$C_6$)-alkyl, or b) fractionating a compound of the formula I which has been prepared by process a) and which, by reason of its chemical structure, occurs in enantiomeric or stereoisomeric forms, by salt formation with enantiomerically pure acids or bases, chromatography on chiral stationary phases or derivatization using chiral enantiomerically pure compounds such as amino acids, separation of the diastereomers obtained in this way, and elimination of the chiral auxiliary group, into the pure enantiomers, or fractionating the stereoisomers by chromatography, or c) hydrolyzing a compound of the formula I which has been prepared as in a), where at least one $R^1$, $R^2$ or $R^3$ is a radical of the formula II or III, to the corresponding phenol, or d) carrying out the reaction of process c) in the presence of sodium bicarbonate, e) hydrolyzing a compound of the formula I which has been prepared as in a), where $R^5$ is a radical of the formula VI and/or at least one $R^1$, $R^2$ or $R^3$ is a radical —O—($C_1$–$C_{12}$)-alkyl-C(O)—O—($C_1$–$C_{12}$)-alkyl, to the carboxylic acid, or f) carrying out the reaction of process e) in the presence of an ethanolic potassium hydroxide solution or of a hydrochloric acid solution, or g) hydrogenating a compound of the formula I which has been prepared as in a) and contains one or two double bonds with α.) hydrogen and a Pd/C catalyst or Raney nickel or β.) sodium borohydride, or h) hydrolyzing a monoalkyl or dialkyl phosphonate of the formula i which has been prepared as in a) to the phosphonic monoester or to the phosphonic acid, carrying out the cleavage of the phosphonic ester in the presence of bromotrimethylsilane in dichloromethane, or i) either isolating the compound of the formula I which has been prepared by process a), b), c), e), g), h), k) or l) in free form or, if acidic or basic groups are present, converting it into physiologically tolerated crystalline salts, or k) reacting a compound of the formula I where at least one of the radicals $R^1$, $R^2$ or $R^3$ is a hydroxyl radical with a compound of the formula XI (XI) X—$R^{13}$, where X is halogen or substituted phenylsulfonyloxy, and $R^{13}$ is defined as for $R^1$ 1) to 12) in formula I, after treatment with sodium hydride or in the presence of potassium carbonate in acetonitrile, dimethylformamide or cyclic ketones, or with $R^{13}$COCl or

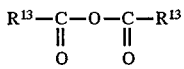

where $R^{13}$ is defined as in formula XI, where appropriate with catalysis by nitrogen bases such as pyridine, to give the corresponding phenol ethers or phenol esters, l) hydrogenating a compound of the formula I which has been prepared by process a), where $R^5$ is CN, in the presence of hydrogen and a Pd/C catalyst or Raney nickel, or m) reacting an amino compound which has been obtained by process l) with a ($C_1$-$C_3$)-alkylcarboxylic anhydride to give the corresponding carboxamide, or n) converting a compound of the formula I which has been prepared by process a), where $R^5$ is —COOH, by esterification into the corresponding carboxylic ester, where the carboxylic acids are converted with oxalyl chloride into the carbonyl chloride, and the latter is reacted with $R^{10}$—OH.

The invention also relates to pharmaceuticals which have an effective content of at least one of a compound of the formula (I)

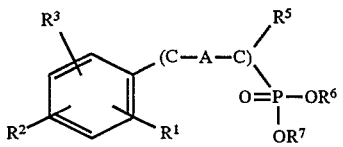

a physiologically tolerated salt thereof, and where appropriate, a stereoisomer thereof, where the radicals $R^1$, $R^2$, $R^3$, $R^5$, R', (C-A-C) and $R^7$ are defined as in formula I, but with inclusion of the provisos, together with a pharmaceutically suitable and physiologically tolerated vehicle, additive and/or other active substance and ancillary substance.

The compounds according to the invention are, by reason of their pharmacological properties, outstandingly suitable for the treatment and prophylaxis of degenerative joint disorders, of rheumatic disorders accompanied by cartilage breakdown, such as chronic rheumatoid arthritis, joint trauma and chondrolysis as a consequence of prolonged immobilization of the joint, of inflammations, septic shock, disorders with impaired leukocyte adhesion, disorders caused by an elevated concentration of tumor necrosis factor alpha, such as cachexia or Crohn's disease.

Examples of degenerative joint disorders are osteoarthritis, other rheumatic disorders with cartilage breakdown, rheumatoid arthritis, chondrolysis after joint trauma, for example, after meniscus or patella injuries or torn ligaments, or chondrolysis associated with prolonged immobilization of joints.

The Pharmaceuticals according to the invention can be administered orally, intramuscularly, periarticularly, intraarticularly, intravenously, intraperitoneally, subcutaneously or rectally.

The invention also relates to a process for the production of a pharmaceutical, which comprises converting at least one compound of the formula I into a suitable dosage form with a pharmaceutically suitable and physiologically tolerated vehicle and, where appropriate, other suitable active substances, additives or ancillary substances.

Examples of suitable solid or liquid pharmaceutical presentations are granules, powders, coated tablets, tablets, (micro)capsules, suppositories, syrups, solutions, suspensions, emulsions, drops or injectable solutions and products with protracted release of active substance, which are produced using conventional aids such as vehicles, disintegrants, binders, coating agents, swelling agents, glidants or lubricants, flavorings, sweeteners and solubilizers. Ancillary substances which may be mentioned are magnesium carbonate, titanium dioxide, lactose, mannitol and other sugars, talc, lactalbumin, gelatin, starch, cellulose and derivatives thereof, animal and vegetable oils such as fish liver oil, sunflower, arachis or sesame oil, polyethylene glycols and solvents such as, for example, sterile water and monohydric or polyhydric alcohols, for example glycerol.

The pharmaceuticals are preferably produced and administered in dosage units, each unit containing as active ingredient a particular dose of the compound of the formula I according to the invention. In the case of solid dosage units such as tablets, capsules, coated tablets or suppositories, this dose can be up to about 1000 mg, preferably about 50 to 300 mg, and for injection solutions in ampoule form it is up to about 300 mg, preferably about 10 to 100 mg.

The daily doses indicated for the treatment of an adult patient weighing about 70 kg are, depending on the efficacy of the compounds of the formula I, from about 20 to 1000 mg of active substance, preferably about 100 to 500 mg. However, in some circumstances higher or lower daily doses may also be appropriate. The daily dose can be administered either by single administration in the form of a single dosage unit or else several smaller dosage units or by multiple administration of divided doses at particular intervals.

The structures of all the compounds described hereinafter were proved by elemental analyses, mass spectra, IR and/or $^1$H-NMR spectra. The NMR spectra were obtained on a Varian Associates Inc. Gemini 200 (200 MHz) machine. The chemical shifts are expressed in δ values (ppm [parts per million] low field shift from tetramethylsilane). The HPLC conditions for determining the E/Z stereoisomer ratio are as follows: Analytical column: LiChroCART® 125-4 LichroSper® 100 RP-18 endcapped 5 µm (Merck 1.508.0001) at 1.5 ml/min; eluent A=acetonitrile; eluent B=0.1 molar phosphoric acid. Good separations are obtainable with linear gradients. For this purpose, the solvent content is increased from m % A to n % A over the course of 0 to 10 minutes, followed by isocratic elution with a solvent content of n % A for 5 minutes. The R value [%] indicates the content of the stereomer with the relevant retention time t [min]. Uv (254 nm) detection. Silica gel plates (silica gel 60 $F_{254}$ special 0.25 mm, Riedel-de Haen AG, Seelze) are used for the thin-layer chromatography. "Evaporation under reduced pressure" is carried out with a rotary evaporator (Büchi RE 140) under the conditions recommended by the manufacturer of the apparatus. Column chromatography is carried out on silica gel 60 (particle size 40 to 63 µm, Merck).

The stated yields are not optimized. The numbers stated in parentheses armor the example numbers indicate the numbers of the corresponding compound(s) in Table I.

EXAMPLE 1 (62)

Isopropyl 3-(3,4-dibenzyloxyphenyl)-2-(diethoxyphosphinyl) propenoate (E stereomer)

Chlorotitanium triisopropoxide [(CH$_3$)$_2$CHO]$_3$TiCl (8.1 ml; 0.034 mol) was added dropwise at 0° C. to 50 ml of tetrahydrofuran (THF) and stirred, followed by solutions of 3,4-dibenzyloxybenzaldehyde (8 g; 0.0157 mol) and of triethyl phosphonoacetate (3.52 g; 0.0157 mol), each in 12.5 ml of tetrahydrofuran. After further stirring (30 minutes), a solution of N-methylmorpholine (5.56 ml; 0.05 mol) in THF (25 ml) was added dropwise at 0° C. Stirring was continued for 10 hours after warming to room temperature. Water (40 ml) was then added, and the precipitated titanium dioxide was removed on a suction funnel. The filtrate was extracted three times with 75 ml of diethyl ether each time. The combined organic phases were dried over Na$_2$SO$_4$ and evaporated under reduced pressure. The remaining oil was dried in a kugelrohr apparatus at a temperature of 60° C. and a pressure of 0.02 mm Hg. A pale yellow oil was obtained.

Yield: 6 g (71% of theory)

Content of E stereomer:=93%

HPLC: m=n=20; R=94.2; t=12.34

$^1$H-NMR: (in CDCl$_3$; 200 MHz): δ=8.0 (d; <0.1 H; J=43 Hz), 7.2 (m; 14 H), 5.15 (m; 5 H), 4.15 (m; 4 H), 1.36 (t; 6 H), 1.24 (d; 6 H)

Elemental analysis for C$_{30}$H$_{35}$O$_7$P (molecular weight (MW)=538.58 g/mol):

calculated: C 66.90 H 6.56 P 5.75 found: C 67.46 H 6.72 P 5.58

EXAMPLE 2 (57)

Ethyl 3-(3,4-diacetoxyphenyl)-2-(diethoxyphosphinyl) propenoate

A solution of titanium tetrachloride (7.74 ml; 0.0706 mol) in 16 ml of dry dichloromethane was added dropwise, starting at 0° C., to 100 ml of absolute tetrahydrofuran (THF) with exclusion of moisture and with vigorous stirring. The exothermic reaction was allowed to progress to 15° C. After renewed cooling to 0° C., 3,4-diacetoxybenzaldehyde (8 g; 0.035 mol; E. Pascu and L. v. Vargha, Ber. dtsch. Chem. Ges., 59: 2817, 1926) and triethyl phosphonoacetate (7.38 g; 0.035 mol) were added. Then, after 30 minutes, with efficient cooling at 0° C., a solution of dry N-methylmorpholine (14.4 ml; 0.131 mol) in 30 ml of absolute tetrahydrofuran was added dropwise. The mixture was allowed slowly (3 hours) to reach room temperature and left to stand for at least 30 minutes but not more than overnight. Working up entailed hydrolysis with water (40 ml), filtration with suction and repeated extraction of the filtrate by shaking with diethyl ether. The combined organic phases were washed with saturated brine and dried over sodium sulfate. An oil remained after concentration under reduced pressure and was chromatographed on silica gel (with ethyl acetate and dichloromethane as eluent). This resulted in a pale oil.

Yield: 8.9 g (58.9% of theory)

Content of E stereomer:≧96% (according to HPLC and NMR data, see below)

HPLC: m=25; n=40; R=96.03; t=6.21

$^1$H-NMR: (in CDCl$_3$; 200 MHz): δ=8.1 (d; <0.1 H; J=43 Hz), 7.55 (d; 1 H; J=24 Hz), 7.25 (m; 3 H), 4.20 (m; 6 H), 2.3 (S; 6 H), 1.39 (t; 6 H); 1.24 (t; 3 H)

Elemental analysis for C$_{19}$H$_{25}$O$_9$P (MW=428.37 g/mol):

calculated C 53.28 H 5.89 P 7.23 found C 52.70 H 5.62 P 7.60

EXAMPLE 3 (47)

Ethyl 2-(diethoxyphosphinyl)-3-(3,4-dihydroxyphenyl) propenoate

Ethyl 3-(3,4-diacetoxyphenyl)-2-(diethoxyphosphinyl) propenoate (3 g; 0.007 mol) from Example 2 was stirred under protective gas with 60 ml of saturated sodium bicarbonate solution at room temperature for 10 hours. The mixture was acidified with 5N hydrochloric acid and extracted by shaking with dichloromethane. The organic phase was dried over sodium sulfate and evaporated under reduced pressure. The residue was dried in a kugelrohr apparatus at a temperature of 60° C. and a pressure of 0.02 mm Hg. This resulted in a brown oil. Yield: 1.9 g (80% of theory)

Elemental analysis for C$_{15}$H$_{21}$O$_7$P (MW=344.30 g/mol):

calculated C 52.33 H 6.16 P 8.99 found C 52.17 H 6.67 P 9.23

EXAMPLE 4 (29)

2-(Diethoxyphosphinyl)-3-(3,4-dimethoxyphenyl) propionic acid

Isopropyl 2-(diethoxyphosphinyl)-3-(3,4-dimethoxyphenyl) propionate (0.51 g; 0.0013 mol; Table 1, No. 60) was stirred in 5 ml of 1M potassium hydroxide solution and 5 ml of ethanol at room temperature for 10 hours. The mixture was acidified with 5N hydrochloric acid, most of the ethanol was removed by evaporation under reduced pressure, and the residue was diluted with 10 ml of water and extracted by shaking several times with 5 ml of dichloromethane each time. The combined organic phases are dried over sodium sulfate and evaporated to dryness under reduced pressure. The remaining residue was dried in a kugelrohr apparatus at a temperature of 60° C. and a pressure of 0.02 mm Hg. This resulted in a pale viscous oil.

Yield: 0.35 g (78% of theory)

MS (EI) m/z 347 (M+H$^-$); (C$_{15}$H$_{23}$O$_7$P; MW=346.32 g/mol)

EXAMPLE 5 (61)

Ethyl 3-(3,4-diacetoxyphenyl)-2-(diethoxyphosphinyl) propionate (rac.)

Ethyl 3-(3,4-diacetoxyphenyl)-2-(diethoxyphosphinyl) propenoate (4.2 g; 0.0098 mol) from Example 2 was hydrogenated in 200 ml of absolute ethanol over 0.5 g of 10 percent Pd/C catalyst in a Parr hydrogenation apparatus under an initial pressure of 3.45 bar until hydrogen uptake was finished. The catalyst was filtered off and the filtrate was evaporated under reduced pressure. The residue was chromatographed on silica gel with ethyl acetate. Drying in a kugelrohr apparatus at a temperature of 60° C. and a pressure of 0.02 mm Hg resulted in a pale oil. Yield: 3.2 g (76% of theory)

MS (CI) m/z 431; (C$_{19}$H$_{27}$O$_9$P; MW=430.39 g/mol)

EXAMPLE 6 (22)

Isopropyl 3-(3,4-dibenzyloxyphenyl)-2-(diethoxyphosphinyl) propionate

A solution of sodium borohydride 0.095 g; 0.0025 mol) in 10 ml of ice-water was added dropwise to a solution of isopropyl 3-(3,4-dibenzyloxyphenyl)-2-(diethoxyphosphinyl)propenoate (2.5 g; 0.0046 mol) from Example 1 in 70 ml of ethanol at 0° C. Stirring was continued for 2 hours after warming to room temperature. The reaction mixture was acidified with 5N hydrochloric acid and extracted several times with dichloromethane (15 ml each time). The combined organic phases were dried over sodium sulfate and evaporated under reduced pressure. The remaining pale oil was pure by thin-layer chromatography ($SiO_2$; $CH_2Cl_2$: EtOAC=7:3).

Yield: 1.8 g (72.4% of theory)

MS (EI) m/z 541; ($C_{30}H_{37}O_7P$; MW=540.59 g/mol)

EXAMPLE 7 (51)

Ammonium hydrogen 2-(3,4-dibenzyloxybenzylidene)-isopropoxycarbonylmethanephosphonate Isopropyl 3-(3,4-dibenzyloxyphenyl)-2-(diethoxyphosphinyl)propenoate (2 g; 0.0037 mol) from Example 1 was stirred together with bromotrimethylsilane (0.52 ml; 0.004 mol) in dichloromethane (70 ml) at room temperature for 3 days. To complete the reaction, bromotrimethylsilane (0.52 ml; 0.004 mol) was again added and stirring was continued at room temperature (6 hours). Ammoniacal ethanol was added and then the mixture was evaporated under reduced pressure. The partly crystalline residue was dispersed with isopropanol. The precipitate was removed by filtration, and the mother liquor was concentrated under reduced pressure in a rotary evaporator to about half the volume. Filtration of the precipitate formed and drying thereof resulted in a solid substance with melting point 187° to 188° C. Yield: 1 g (54% of theory)

MS (FAB), (M+Na$^+$) m/z 505.2; $C_{16}H_{27}O_7P+Na^+$; (MW=505.41 g/mol)

NMR (200 MHz, DMSO): δ=7.2 to 7.5 (m; 10 H), 6.8 to 7.1 (m; 4 H), 5.08 (d; 4 H; J=16.7 Hz), 4.95 (m; 1 H), 1.15 (d; 6 H; J=6.2 Hz)

EXAMPLE 8 (8)

Isopropyl 3-[3, 5-dimethoxy-4-(4-methoxybenzyloxy)phenyl]-2-(dimethoxyphosphinyl)propenoate Isopropyl 3-(3,5-dimethoxy-4-hydroxyphenyl)-2-(dimethoxy-phosphinyl)propenoate (4 g; 0.01 mol; Table 1, No. 10) was dissolved in 60 ml of acetonitrile, and potassium carbonate (4.45 g; 0.032 mol) and 4-methoxybenzyl chloride (1.4 ml; 0.011 mol) were added and the mixture was initially stirred at room temperature for 8 hours. To complete the reaction, 0.7 ml of 4-methoxybenzyl chloride was added, followed by stirring for 4 hours, after which the result of a thin-layer chromatography showed that the reaction was complete. The filtrate after removal of potassium carbonate by filtration was evaporated to dryness under reduced pressure, and the residue is chromatographed ($SiO_2$; $CH_2Cl_2$: AcOEt=8:2). This resulted in a slowly crystallizing oil which, on solidification, had a melting point of 68° to 69° C.

Yield: 4.4 g (88.9% of theory)

Elemental analysis for $C_{24}H_{31}O_9P$ (MW=494.48 g/mol):

calculated C 58.30 H 6.33 P 6.26 found C 58.10 H 6.70 P 6.30

EXAMPLE 9 (72)

Isopropyl 2-(dimethoxyphosphinyl)-3-(3-hexyloxy-4-methoxyphenyl)propenoate

Isopropyl 2-(dimethoxyphosphinyl)-3-(3-hydroxy-4-methoxy-phenyl)propenoate (2 g; 0.0058 mol; Table 1, No. 26), 1-bromohexane (0.85 ml; 0.006 mol), 30 ml of dimethylformamide (DMF) and potassium carbonate (ground, 0.89 g; 0.0065 mol) were mixed and stirred at room temperature for 6 hours. The filtrate after removal of the inorganic salts was evaporated under reduced pressure. Residues of DMF were removed from the resulting oily residue in a kugelrohr apparatus at 70° C./0.02 mm Hg, and it was then chromatographed on silica gel eluting with a dichloromethane:ethane acetate (8:2) mixture. This resulted in a pale oil. Yield: 3.6 g (72.5% of theory)

Elemental analysis for $C_{21}H_{33}O_7P$ (MW=428.47 g/mol)

calculated C 58.87 H 7.78 P 7.23 found C 58.5 H 7.7 P 7.0

HPLC: m=20, n=60, R=96.67, t=11.549; NMR (200 MHz, CDCl$_3$): δ=8.1 (d; <0.1 H; J=42 Hz), 7.53 (d; 1 H; J=23 Hz), 6.8 to 7.3 (m; 4 H), 5.2 (sept; 1 H), 3.6 to 4.1 (m; 12 H), 1.2 to 2.0 (m; 15 H)

EXAMPLE 10 (37 and 38)

Z- and E-2-(diethoxyphosphinyl)-3-(3,4-dimethoxyphenyl) acrylonitrile

As in Example 1, 3,4-dimethoxybenzaldehyde (21 g; 0.123 mol) was reacted with diethyl cyanomethanephosphonate (22.32 g; 0.123 mol), chlorotitanium triisopropoxide (61.5 ml; 0.26 mol) and N-methylmorpholine (28 ml; 0.25 mol) in 300 ml of tetrahydrofuran and worked up. It was possible by chromatography on silica gel with the eluent dichloromethane/ethyl acetate (2:1) to separate the two stereomeric forms of the title compound as substantially pure fractions.

1.) Z stereomer (2.6 g):

Elemental analysis for $C_{15}H_{20}NO_5P$ (MW=325.30 g/mol):

calculated C 55.38 E 6.21 N 4.31 P 9.52 found C 55.77 E 6.54 N 4.51 P 9.27

HPLC: m=5, n=50, R=81.72, t=10.904

NMR (200 MHz, CDCl$_3$): δ=6.8 to 8.0 (m, 4 H, including: 7.80 (d; 1 H; J=40 Hz)), 4.1 to 4.3 (m; 4 H), 4.95 (s; 6 H), 1.3 (t; 6 H)

2.) Stereomer mixture (19 g)

3.) E stereomer (4.5 g):

Elemental analysis for $C_{15}H_{20}NO_5P$ (MW=325.30 g/mol):

calculated C 55.38 E 6.21 N 4.31 P 9.52 found C 55.53 E 6.56 N 4.41 P 9.57

HPLC: m=5, n=50, R=98.83, t=11.549

NMR (200 MHz, CDCl$_3$): δ=7.90 (d; 1 H; J=21 Hz), 6.8 to 7.8 (m, 3 H), 4.1 to 4.4 (m; 4 H), 3.9 (s; 6 H), 1.4 (t; 6 H)

EXAMPLE 11 (19)

Diethyl {2-acetylamino-1-[(3,4-dimethoxyphenyl)methyl]ethyl}phosphcnate 2-(Diethoxyphosphinyl)-3-(3,4-dimethoxyphenyl) acrylonitrile (Table 1, Nos. 37/38; stereomer mixture; 4 g;

0.0123 mol) was dissolved in acetic anhydride (100 ml) and hydrogenated in a Parr hydrogenation apparatus in the presence of Raney nickel catalyst (0.6 g) and sodium acetate (anhydrous; 1.2 g; 0.015 mol) under an initial pressure of 3.45 bar until hydrogen uptake was complete. Sodium acetate and catalyst were filtered off, and the filtrate was evaporated under reduced pressure (30 mbar). The residue was chromatographed on silica gel (eluent: ethyl acetate:ethanol, 9:1). This resulted in the title compound as a pure fraction of 1.4 g (30.5% of theory)

MS (ES) m/z 374 (M+H+); $C_7H_{28}NO_6P$; (MW=373.39 g/mol)

EXAMPLE 12 (45)

3-(3,4-Diacetoxyphenyl)-2-(diethoxyphosphinyl) propionitrile 3-(3,4-Diacetoxyphenyl)-2-(diethoxyphosphinyl) acrylonitrile (Table 1, No. 56; 2.5 g; 0.0066 mol) was hydrogenated in 100 ml of acetic anhydride over 0.5 g of 10 percent Pd/C catalyst in a Parr hydrogenation apparatus under an initial pressure of 3.45 bar until hydrogen uptake was complete (16 hours), adding an additional 0.3 g of catalyst after 8 hours had elapsed. Finally, the catalyst was filtered off and the filtrate was evaporated under reduced pressure. The residue was chromatographed on silica gel, eluted with the solvent mixture dichloromethane:ethyl acetate (7:3). This results in the title compound as a pale oil in a yield of 1.7 g (67.7% of theory).

MS (EI) m/z 384 (M+H+); $C_{17}H_{22}NO_7P$; (MW=383.34 g/mol)

EXAMPLE 13 (6)

1,4-Bis-{[5-(2-dimethoxyphosphinyl-2-isopropoxycarbonyl-ethenyl)-2-methoxyphenoxy] methyl}benzene 3-Hydroxy-4-methoxybenzaldehyde (3 g; 0.0197 mol), α,α'-dibromo-p-xylene (2.3 g; 0.009 mol) and powdered potassium carbonate (4 g; 0.03 mol) were stirred in acetonitrile (20 ml) at room temperature for 6 hours. The reaction mixture was then filtered. Only small amounts of product were to be found in the filtrate after evaporation under reduced pressure. The residue on the filter was taken up in water and extracted by shaking several times with dichloromethane. The combined organic phases were dried over sodium sulfate and evaporated under reduced pressure, finally at 60° and 0.03 mbar. This resulted in 1, 4-bis-[(5-formyl-2-methoxyphenoxy)methyl]benzene in the form of white crystals (2.2 g; 54.9% of theory) with melting point 180° to 181° C.

$^1$H-NMR (in $CDCl_3$, 200 MHz): δ=9.81 (s; 2 H), 6.9 to 7.6 (m; 10 H), 5.19 (s; 4 H), 3.96 (s; 6 H)

Chlorotitanium triisopropoxide (1.6 ml; 0.00984 mol) was added dropwise at 0° C. to tetrahydrofuran (75 ml). At the same temperature, a solution of the 1,4-bis-[(5-formyl-2-methoxyphenoxy)-methyl]-benzene obtained above (2 g; 0.00492 mol) and a solution of trimethyl phosphonoacetate (1.6 mi; 0.00984 mol) in 10 ml of dry tetrahydrofuran were then added dropwise under an argon atmosphere. After stirring at 0° C. for half an hour, a solution of N-methylmorpholine (2.2 ml; 0.0196 mol) in tetrahydrofuran-(5 ml) was added. The reaction mixture was allowed to warm to room temperature and was stirred for a further 8 hours. Then water (20 ml) was added. The precipitated salts were filtered off with suction; and the filtrate was extracted by shaking several times with diethyl ether. The organic phases were combined, dried over sodium sulfate and evaporated under reduced pressure. The resulting yellow oil was chromatographed on silica gel (eluent: ethyl acetate). This resulted in the title compound as a pure fraction in a yield of 1.5 g (38.6% of theory) in the form of a pale oil.

MS (FAB) m/z 791.3 (M+H+); $C_{38}H_{48}O_{14}P_2$; (MW= 790.75 g/mol)

HPLC: m=40, n=80, R=49.33, t=8.717

EXAMPLE 14 (5 and 4)

1,4-Bis-{[5-(2-diethoxyphosphinyl-2-cyanoethenyl)-2-methoxyphenoxy]methyl)benzene (and as byproduct: 3-[3-(bromomethyl)benzyloxy)-4-methoxyphenyl]-2- -(diethoxyphosphinyl) acrylonitrile)

2-(Diethoxyphosphinyl)-3-(3-hydroxy-4-methoxyphenyl)acrylonitrile (Table 1, No. 77; 6 g; 0.019 mol), α,α'dibromo-p-xylene (2.5 g; 0.0096 mol), potassium carbonate (1.45 g; 0.011 mol), a few crystals of potassion iodide as catalyst and acetonitrile (60 ml) were stirred together at room temperature in analogy to Example 8 (4 days). Then further potassium carbonate (1.3 g; 0.009 mol) was added and stirring was continued at 50° C. (1 day). After filtration, the filtrate was evaporated under reduced pressure and the residue was chromatographed on silica gel (eluent: dichloromethane:ethyl acetate:petroleum ether, 6:2:2). The first pure fraction collected was 3-[3-(bromomethyl)benzyloxy)-4-methoxyphenyl]-2-(diethoxyphosphinyl) acrylonitrile with melting range 90° to 107° C. (Table 1, No. 4) in an amount of 0.7 g (7.35% of theory).

MS (ES) m/z 494.3 (M+H+); $C_{22}H_{25}BrNO_5P$; (MW= 494.33 g/mol)

HPLC: m=40, n=80, R=81.37, t=6.853

Elution of a small amount of the initial nitrile was followed by the title compound as another pure fraction in a yield of 2.7 g (38.6% of theory) with melting point 166° to 169° C.

Elemental analysis for $C_{36}H_{42}N_2O_{10}P_2$ (MW=724.69 g/mol)

calculated C 59.67 H 5.85 N 3.87 P 8.55 found C 60.0 H 5.7 N 3.9 P 8.1

HPLC: m=40, n=80, R=88.27, t=8.635

EXAMPLE 15 (33 and 34)

2-(Diethoxyphosphinyl)-3-(3,4-dimethoxyphenyl) propyl-amine(I) and 2-(diethoxyphosphinyl)-3-(3,4-dimethoxy-phenyl)propiononitrile(II)

2-(Diethoxyphosphinyl)-3-(3,4-dimethoxy-phenyl) acrylonitrile, as mixture of E and Z stereomers (Table 1, Nos. 37 and 38; 4 g; 0.012 mol), was hydrogenated in 100 ml of ethanol over 0.6 g of 10 percent Pd/C catalyst in a Parr hydrogenation apparatus under an initial pressure of 3.45 bar until hydrogen uptake was complete. The catalyst was filtered off and the filtrate was evaporated under reduced pressure. The residue was chromatographed on silica gel with ethyl acetate/dichloromethane (9:1). The pure fractions obtained were 0.7 g (17.2% of theory) of title compound I;

Elemental analysis for $C_{15}H_{26}NO_5P$ (MW=331.35 g/mol):

calculated: C 54.37 H 7.93 N 4.23 found: C 54.6 H 7.4 N 4.1

IR (KBr): no band at 2240 $cm^1$ and 1.15 g (28.6% of theory) of title compound II, likewise as oil.

Elemental analysis for $C_{15}H_{22}NO_5P$ (MW=327.32 g/mol):

calculated: C 55.04 E 6.79 N 4.28 found: C 54.6 E 7.0 N 4.5

MS (EI+m/z 328 (M +H$^+$) IR (KBr): inter alia 2240 cm$^{-1}$

EXAMPLE 16 (67)

3-(3,4-Dibenzyloxyphenyl)-2-(dimethoxyphosphinyl) propenoic acid

Chlorotitanium triisopropoxide [(CH$_3$)$_2$CHO]$_3$TiCl (15 ml; 0.063 mol) was added to tetrahydrofuran (anhydrous, 95 ml) which had been cooled to 2° C. and was maintained under an argon atmosphere in such a way that a brief increase in temperature to 10° C. was not exceeded. To this was added dropwise a solution of dimethyl carboxymethylphosphonate (2.6 g; 0.0155 mol) in tetrahydrofuran, initially at 2° C. and towards the end at 5° C. It was also possible alternatively to add the sodium or potassium salt of dimethyl carboxymethylphosphonate as powder or suspension in THF. The heterogeneity of the reaction mixture meant that it was expedient then to triple the stirring times before adding the following reagents. After stirring for 10 minutes, a solution of 3,4-dibenzyloxybenzaldehyde (5 g; 0.016 mol) was added, likewise at 2° C., and the mixture was stirred at this temperature for a further half an hour. Then N-methylmorpholine was added, still at 2° C., and the mixture is allowed to reach room temperature over about 3 hours. After standing for 15 hours, it was acidified to pH 2 to 3 with 5N hydrochloric acid and extracted by shaking several times with diethyl ether. The combined ethereal solutions were concentrated under reduced pressure, taken up in dichloromethane and separated from the remaining water. After drying over sodium sulfate and evaporation under reduced pressure, the oily residue was chromatographed on silica gel (elution with ethyl acetate/dichloromethane/glacial acetic acid; 3.5:6:0.5). This resulted in the title compound as a viscous oil in a yield of 4.6 g (62.6% of theory).

MS (FAB) m/z 469.2 (M+H$^+$); $C_{25}H_{25}O_7P$; (MW=468.45 g/mol)

HPLC: m=20, n=80, R=85.70, t=12.888

EXAMPLE 17 (79)

Isopropyl 3-(3,4-dibenzyloxyphenyl)-2-(diethoxyphosphinyl)propenoate (Z stereomer)

A solution of triethyl phosphonacetate (2.1 g; 0.00094 mol) in 15 ml of tetrahydrofuran was added drop-wise to a suspension of sodium hydride (0.23 g; 0.0094 mol) in 70 ml of tetrahydrofuran at room temperature under an argon atmosphere and stirred until a clear solution was produced. The reaction solution was then heated under reflux for 1 hour, cooled to −78° C., and chlorotitanium triisopropoxide (2.25 ml; 0.0094 mol) was added. The mixture was allowed to reach room temperature and is then stirred for 1.5 hours. 3,4-Dibenzyloxy-benzaldehyde (3 g; 0.0094 mol) was dissolved in 15 ml of tetrahydrofuran and added dropwise to the above mixture. The reaction mixture was stirred for four hours and then poured into dilute hydrochloric acid and extracted several times with diethyl ether. The combined organic phases were dried over sodium sulfate and evaporated under reduced pressure. The oily residue was dried in a kugelrohr apparatus at 60° C./0.02 mm Hg. Subsequent chromatography on silica gel with dichloromethane/ethyl acetate (4:1) afforded two main fractions:

1.) 0.1 g of a pale oil (predominantly E stereomer, Table 1, No. 62)

2.) 2 g of the title compound as pale oil (39.5% of theory).

Elemental analysis for $C_{30}H_{35}O_7P$ (MW=538.58 g/mol):

calculated: C 66.90 H 6.54 P 5.75 found: C 66.3 H 6.3 P 5.5

HPLC: m=50, n=80, R=90.34, t=5.152

NMR (200 MHz, CDCl$_3$): δ=8.0 (d; 0.9 H; J=40 Hz), 6.7 to 7.6 (m; >13 H incl. proportion of E stereomer and CDCl$_3$), 5.05 to 5.25 (m; 5 H), 3.9 to 4.3 (m; 4 H), 1.1 to 1.4 (m; 12 H)

EXAMPLE 18 (93)

Isopropyl 3-(3-acetoxy-4-methoxyphenyl)-2-(dimethoxyphosphinyl)propenoate

Isopropyl 2-(dimethoxyphosphinyl)-3-(3-hydroxy-4;-methoxy-phenyl)propenoate (Table 1, No. 26; 2 g; 0.0058 mol) was stirred in 15 ml of acetic anhydride with 2 drops of pyridine initially at 10° C. for 10 minutes and then at room temperature for 6 hours. 15 ml of water were added to hydrolyze the excess acetic anhydride while stirring. The reaction mixture was extracted by shaking several times with dichloromethane. The combined organic phases were dried over sodium sulfate and evaporated under reduced pressure. The remaining oil was dried in a kugelrohr apparatus at 60° C./0.02 mm Hg. This resulted in 1.7 g (75.9 % of theory).

MS (DCI) m/z 495.2 (M+H$^+$)

HPLC: m=5, n=50, R=92.00, t=11.417

EXAMPLE 19 (94)

Isopropyl 3-(4-diethoxyphosphinylmethoxy-3-methoxyphenyl)-2-(dimethoxyphosphinyl) propenoate Isopropyl-2-(dimethoxyphosphinyl)-3-(4-hydroxy-3-methoxyphenyl)propenoate (Table 1, No. 69; 2 g; 0.0058 mol) and sodium hydride (0.144 g; 0.006 mol) were stirred in 10 ml of dimethyl sulfoxide at room temperature for 20 minutes. Then a solution of diethyl 4-chlorophenylsulfonyloxy methylphosphonate [Org. Synth., 64: 80, 1985] (2.23 g; 0.0065 mol) in 10 ml of dimethyl sulfoxide was added. The reaction mixture was stirred at room temperature for 10 hours and then evaporated under reduced pressure. The remaining oil was chromatographed on silica gel with ethyl acetate:ethanol (9.5:0.5). 0.4 g (16 % of theory) of a pale oil is obtained.

MS (DCI) m/z 495.2 (M+H$^+$)

HPLC: m=5, n=50, R=94.21, t=11.346

EXAMPLE 20

Isopropyl 3-(4-carboxymethoxy-3-methoxyphenyl)-2-(dimethoxyphosphinyl)propenoate (E stereomer)

Isopropyl 3-(4-tert-butoxycarbonylmethoxy-3-methoxyphenyl):)-2-(dimethoxyphosphinyl) propenoate (Table 1, No. 91; 0.5 g; 0.011 mol) was stirred in 10 ml of 5N hydrochloric acid at 60° C. for 4 hours and then cooled to room temperature. The precipitated crystals were filtered off with suction, washed several times with water and dried. This resulted in 0.27 g (61.5% of theory) with melting point 156°–158° C.

MS (FAB) m/z 403.2 (M+H )

HPLC: m=15, n=70, R=92.44, t=6.677

EXAMPLE 21 (110)

2-(4-morpholinyl)ethyl 3-(3,4-dimethoxyphenyl)-2-(dimethoxyphosphinyl) propenoate 3-(3,4-Dimethoxyphenyl)-2-(dimethoxy-phosphinyl) propenoic acid (Table 1, No. 107; 2.3 g; 0.0069 mol) was suspended in toluene (30 ml), and a solution of oxalyl chloride (0.6 ml; 0.007 mol) in 2 ml of toluene was added, followed by 3 drops of dimethylformamide. The carboxylic acid dissolved. The mixture was then stirred for 2 hours and evaporated under reduced pressure. The resulting yellow oil showed, inter alia, an IR band at 1775 cm$^1$ and was reacted further as crude product. Yield: 2.2 g (crude The carbonyl chloride obtained in this way was dissolved in 70 ml of acetonitrile. N-(2-hydroxyethyl)morpholine was added and the mixture was stirred for 10 hours. The reaction solution was evaporated under reduced pressure. The residue was taken up in 50 ml of dichloromethane and washed with saturated sodium bicarbonate solution. After drying over sodium sulfate and evaporation under reduced pressure, the remaining oil was purified by chromatography on silica gel (ethyl acetate:ethanol=8:2). This resulted in 0.6 g (20% of theory) of a viscous oil.

MS (FAB) m/z 430.2 (M+H$^+$)

HPLC: m=0, n=70, R=84.02, t=7.107

TABLE 1

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 1 | (structure) | Calc. for $C_{26}H_{42}NO_5P$: C 65.11 H 8.84 N 2.92 P 6.46 found: C 65.2 H 9.0 N 3.1 P 6.3 HPLC (m = 30, n = 80; R = 93.0; t = 17.794) | 9 |
| 2 | (structure) | MS (DEI) m/z 390 | 5 |
| 3 | (structure) | MS (DEI) m/z 370 HPLC (m = 40, n = 80; $R^1$ = 68.11; t = 1.698; $R^2$ = 31.56; t = 1.883) | 1 |
| 4 | (structure) | MS (ES) m/z 494.3 (M + H$^+$) HPLC (m = 40; n = 80; R = 81.37; t = 6.853) | 14 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|----|---------|---------------------|-------|
| 5 | 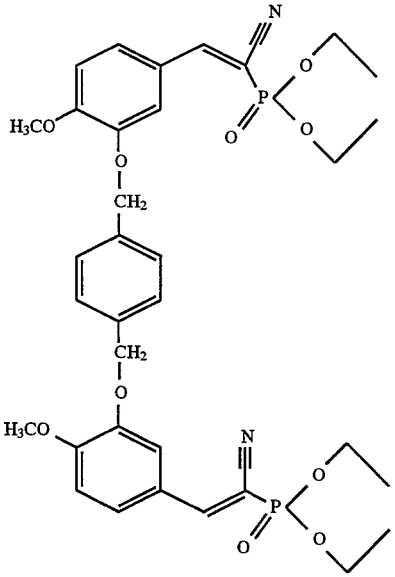 | Calc. for $C_{36}H_{42}N_2O_{10}P_2$:<br>C 59.67 H 5.85 N 3.87 P 8.55<br>found:<br>C 60.0 H 5.7 N 3.9 P 8.1<br>HPLC (m = 40; n = 80;<br>R = 88.27; t = 8.635 | 14 |
| 6 | 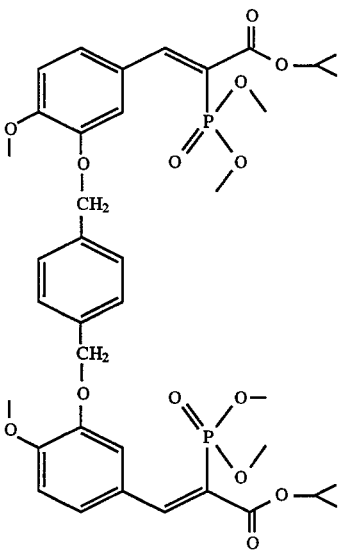 | MS (FAB) m/z 791.3 (M + H$^+$)<br>HPLC (m = 40; n = 80;<br>R = 49.331; t = 8.717) | 13 or 14 |
| 7 | 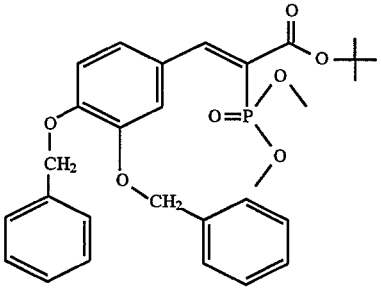 | Calc. for $C_{29}H_{33}O_7P$:<br>C 66.4 H 6.35 P 5.90<br>found:<br>C 65.3 H 6.1 P 6.0<br>HPLC (m = 40; n = 80;<br>R = 76.91; t = 10.769) | 1 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 8 | (structure) | Calc. for $C_{24}H_{32}O_9P$:<br>C 58.30 H 6.33 P 6.26<br>found:<br>C 58.10 H 6.7 P 6.3<br>HPLC (m = 40; n = 80;<br>R = 98.49; t = 7.014) | 8 |
| 9 | (structure) | Calc. for $C_{21}H_{24}NO_1P$:<br>C 62.84 H 6.04 N 3.49 P 7.71<br>found:<br>C 62.8 H 6.1 N 3.5 P 7.7<br>HPLC (m = n = 50;<br>R = 90.93; t = 7.200) | 8 |
| 10 | (structure) | MS (EI) m/z 375 (M + H+)<br>HPLC (m = 50; n = 80;<br>R = 99.30; t = 1.183) | 1 |
| 11 | (structure) | MS (EI) m/z 480 (M + H+) | 6 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|----|---------|---------------------|-------|
| 12 | (structure) | MS (EI) m/z 361 (M + H$^+$) | 5 |
| 13 | (structure) | Calc. for C$_{16}$H$_{23}$O$_9$P:<br>C 53.64 H 6.48 P 8.64<br>found:<br>C 53.0 H 6.0 P 8.4<br>HPLC (m = 50; n = 80;<br>R = 97.77; t = 1.749) | 1 |
| 14 | (structure) | Calc. for C$_{22}$H$_{27}$O$_7$P:<br>C 60.83 H 6.28 P 7.13<br>found:<br>C 60.5 H 6.2 P 7.0<br>HPLC (m = 50; n = 80;<br>R = 98.20; t = 3.222) | 1 |
| 15 | (structure) | Calc. for C$_{16}$H$_{23}$O$_9$P:<br>C 53.63 H 6.48 P 8.64<br>found:<br>C 53.1 H 6.3 P 8.5<br>HPLC (m = 50; n = 80;<br>R = 90.26; t = 2.007) | 1 |
| 16 | (structure) | MS (FAB) m/z 361.2 (M + H$^+$) | 5 |
| 17 | (structure) | MS (FAB) m/z 376.2 (M + H$^+$) | 5 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 18 | | MS (FAB) m/z 359.2 (M + H$^+$) | 5 |
| 19 | | MS (ES) m/z 374 (M + H$^+$) | 11 |
| 20 | | Calc. for $C_{27}H_{30}NO_5P$:<br>C 67.63 H 6.32 N 2.92 P 6.46<br>found:<br>C 67.9 H 5.2 N 3.2 P 6.3<br>HPLC (m = 50; n = 80;<br>R = 91.80; t = 8.988) | 1 |
| 21 | | Calc. for $C_{10}H_{20}O_7P$:<br>C 58.25 H 7.10 P 7.51<br>found:<br>C 57.6 H 6.70 P 7.4<br>HPLC (m = 50; n = 80;<br>R = 97.63; t = 5.414) | 1 |
| 22 | | MS (EI) m/z 541 (M + H$^+$) | 6 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 23 | | MS (EI) m/z 389 (M + H$^+$) | 5 |
| 24 | | MS (EI) m/z 347 (M + H$^+$) | 5 |
| 25 | | MS (EI) m/z 519 (M + Li$^+$) | 6 |
| 26 | | Calc. for C$_{15}$H$_{21}$O$_7$P:<br>C 52.33 H 6.16 P 8.99<br>found:<br>C 53.1 H 6.1 P 9.1<br>HPLC (m = 50; n = 80;<br>R = 93.68; t = 3.178) | 1 |
| 27 | | Calc. for C$_{28}$H$_{31}$O$_7$P:<br>C 65.88 H 6.13 P 6.06<br>found:<br>C 66.2 H 6.1 P 5.8<br>HPLC (m = 50; n = 80;<br>R = 69.77; t = 7.743) | 1 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 28 | (structure) | Calc. for $C_{16}H_{23}O_7P$:<br>C 53.63 H 6.48 P 8.64<br>found:<br>C 53.2 H 6.5 P 8.4<br>HPLC (m = 50; n = 80;<br>R = 99.04; t = 2.018) | 1 |
| 29 | (structure) | MS (EI) m/z 347 (M + H$^+$) | 4 |
| 30 | (structure) | Calc. for $C_{15}H_{20}NO_5P$:<br>C 55.38 H 6.21 N 4.31 P 9.53<br>found:<br>C 55.5 H 6.2 N 4.3 P 9.4 | 1 |
| 31 | (structure) | Calc. for $C_{17}H_{25}O_8P$:<br>C 52.58 H 6.50 P 7.97<br>found:<br>C 52.1 H 6.4 P 7.8 | 1 |
| 32 | (structure) | Calc. for $C_{16}H_{23}PO_7$:<br>C 53.63 H 6.48 P 8.64<br>found:<br>C 53.9 H 6.2 P 8.6<br>MS (EI) m/z 359 (M + H$^+$) | 1 |
| 33 | (structure) | Calc. for $C_{15}H_{26}NO_5P$:<br>C 54.37 H 7.93 N 4.23<br>found:<br>C 54.6 H 7.4 N 4.1 | 15 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 34 | (structure) | Calc. for $C_{15}H_{22}NO_5P$:<br>C 55.04 H 6.79 N 4.28<br>found:<br>C 54.6 H 7.0 N 4.5<br>MS (EI) m/z 328 (M − H⁺) | 15 |
| 35 | (structure) | Calc. for $C_{17}H_{25}NO_8P$:<br>C 52.58 H 6.50 P 7.97<br>found:<br>C 51.1 H 6.50 P 8.4 | 1 |
| 36 | (structure) | MS (EI) m/z 391 (M + H⁺) | 5 |
| 37 | (structure)<br>Z stereomer | Calc. for $C_{15}H_{20}NO_5P$:<br>C 55.38 H 6.21 N 4.31 P 9.52<br>found:<br>C 55.77 H 6.54 N 4.51 P 9.27<br>HPLC (m = 5; n = 50;<br>R = 81.72; t = 10.904) | 10 |
| 38 | (structure)<br>E stereomer | Calc. for $C_{15}H_{20}NO_5P$:<br>C 55.38 H 6.21 N 4.31 P 9.52<br>found:<br>C 55.53 H 6.56 N 4.41 P 9.57<br>HPLC (m = 5; n = 50;<br>R = 98.83; t = 11.549) | 10 |
| 39 | (structure) | Calc. for $C_{16}H_{23}PO_7$:<br>C 53.63 H 6.48 P 8.64<br>found:<br>C 53.45 H 6.50 P 8.08 | 1 |
| 40 | (structure) | MS (ES⁺) m/z 331 (M + H⁺)<br>(phosphonic acid) | 7 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 41 | | MS (EI) m/z 361 (M + H⁺) | 5 |
| 42 | | Calc. for $C_{15}H_{19}O_7P$: <br> C 52.52 H 5.61 P 9.05 <br> found: <br> C 52.52 H 5.55 P 8.97 | 1 |
| 43 | | MS (ES) m/z 351 (M + Li⁺) | 5 |
| 44 | | Calc. for $C_{15}H_{20}NO_5P$: <br> C 55.38 H 6.21 N 4.31 P 9.52 <br> found: <br> C 55.0 H 6.2 N 4.3 P 9.1 | 1 |
| 45 | | MS (EI) m/z 384 (M + H⁺) | 12 |
| 46 | | MS (EI) m/z 517 (M + H⁺) | 5 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 47 | (structure) | Calc. for $C_{15}H_{21}O_7P$:<br>C 52.33 H 6.16 P 8.99<br>found:<br>C 52.17 H 6.68 P 9.23 | 3 |
| 48 | (structure) | Calc. for $C_{18}H_{27}O_7P$:<br>C 55.95 H 7.06 P 8.02<br>found:<br>C 55.99 H 7.44 P 7.94<br>HPLC ($CH_3CN:H_2O = 35.65$;<br>R = 79.83; t = 8.5) | 1 |
| 49 | (structure) | Calc. for $C_{18}H_{23}O_9P$:<br>C 52.18 H 5.61 P 7.47<br>found:<br>C 51.68 H 5.45 P 7.39 | 2 |
| 50 | (structure) | Calc. for $C_{14}H_{22}NO_7P$:<br>C 48.42 H 6.39 N 4.03 P 8.92<br>found:<br>C 47.85 H 6.42 N 4.00 P 8.82 | 7 |
| 51 | (structure) | MS (FAB), (M + Na$^+$)<br>m/z 505.2 | 7 |
| 52 | (structure) | MS (FAB) m/z 332.2<br>(M$^+$ − 2NH$_3$)<br>Calc. for $C_{14}H_{27}N_2O_7P$:<br>C 45.90 H 7.44 N 7.65 P 8.45<br>found:<br>C 45.66 H 8.16 N 5.82 P 8.16 | 7 |

TABLE 1-continued

*The indicated preparation processes (right-hand column, abbreviation: proc.) for all the compounds listed in Table 1 are analogous or identical to the processes for the examples specified in this column.*

| No | Formula | Physical Properties | Proc. |
|----|---------|---------------------|-------|
| 53 | | MS (CI) m/z 417 (M + H$^+$) | 5 |
| 54 | | Calc. for C$_{16}$H$_{25}$O$_7$P:<br>C 53.34 H 7.01 P 8.59<br>found:<br>C 52.98 H 7.00 P 8.55 | 5 |
| 55 | | MS (FAB) m/z 347.1 (M + H$^+$) | 5 |
| 56 | | Calc. for C$_{17}$H$_{20}$O$_7$NP:<br>C 53.55 H 5.30 N 3.67 P 8.12<br>found:<br>C 52.78 H 5.04 N 3.69 P 8.13 | 2 |
| 57 | | Calc. for C$_{19}$H$_{25}$O$_9$P:<br>C 53.28 H 5.89 P 7.23<br>found:<br>C 52.70 H 5.62 P 7.60 | 2 |
| 58 | | MS (CI) m/z 501 (M + H$^+$) | 2 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 59 | | MS (EI) m/z 387.2 (M + H$^+$)<br>Calc. for $C_{18}H_{27}O_7P$:<br>C 55.95 H 7.06 P 8.02<br>found:<br>C 55.73 H 7.32 P 7.71 | 1 |
| 60 | | Calc. for $C_{18}H_{29}O_7P$:<br>C 55.66 H 7.54 P 7.98<br>found:<br>C 55.01 H 8.06 P 7.66 | 5 |
| 61 | | MS (CI) m/z 431 (M + H$^+$)<br>Calc. for $C_{19}H_{27}O_9P$:<br>C 53.03 H 6.34 P 7.19<br>found:<br>C 52.31 H 6.70 P 7.32 | 5 |
| 62 | | $^1$H-NMR (CDCl$_3$): δ = 8.0(d;<br>J=43Hz; <0.1H), 7.2(m; 14 H),<br>5.15(m; 5H); 4.15(m; 4H), 1.36(t;<br>6H), 1.24(d; 6H)<br>HPLC (m = n = 20;<br>R = 94.92; t = 12.34)<br>Calc. for $C_{30}H_{35}O_7P$:<br>C 66.90 H 6.56 P 5.75<br>found:<br>C 67.46 H 6.72 P 5.58 | 1 |
| 63 | | Calc. for $C_{18}H_{27}O_{11}PS_2$<br>C 42.02 H 5.30 P 6.02 S 12.46<br>found:<br>C 42.09 H 5.17 P 5.99 S 12.3 | 1 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 64 | (structure: 4-methoxy-3-(cyclohexylmethoxy)cinnamate with phosphonate) | Calc. for $C_{22}H_{33}O_7P$: C 59.99 H 7.57 P 7.03 found: C 59.7 H 6.0 P 6.9 HPLC (m = 50; n = 50; R = 97.19; t = 5.652) | 1 |
| 65 | (structure: 4-methoxy-3-(dodecyloxy)cinnamate with phosphonate; $H_3C-(CH_2)_{10}-CH_2$) | Calc. for $C_{27}H_{45}O_7P$ C 63.26 H 8.87 P 6.04 found: C 62.9 H 8.4 P 6.2 HPLC (M = 30; n = 70; R = 97.37; t = 16.362) | 9 |
| 66 | (structure: 2,3-dimethoxy cinnamate with phosphonate) | MS (DCI) m/z 361.3 (M + H$^+$) | 5 |
| 67 | (structure: 4-benzyloxy-3-benzyloxy cinnamic acid with phosphonate, COOH) | MS (FAB) m/z 469.2 (M + H$^+$) HPLC (m = 20; n = 80; R = 85.70; t = 12.888) | 16 |
| 68 | (structure: saturated 4-methoxy-3-(dodecyloxy)phenylpropanoate with phosphonate; $H_3C-(CH_2)_{10}-CH_2$) | MS (DCI) m/z 515.5 (M + H$^+$) | 5 |
| 69 | (structure: 4-hydroxy-3-methoxy cinnamate with phosphonate) | MS (DCI) m/z 345.3 (M + H$^+$) HPLC (m = 10; n = 50; R = 94.11; t = 10.344) | 1 | ns
TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|----|---------|---------------------|-------|
| 70 | (structure: 1,4-benzodioxane substituted with $-CH_2-CH(C\equiv N)-P(=O)(O-)(O-)$) | Calc. for $C_{15}H_{18}NO_5P$:<br>C 55.73 H 5.62 N 4.33 P 9.68<br>found:<br>C 55.00 H 5.5 N 4.7 P 9.4<br>HPLC (m = 30; n = 60;<br>R = 91.99; t = 6.356) | 1 |
| 71 | (structure: phenyl with $CH_2=CH-CH_2-O-$ and $-O-CH_3$ substituents, connected to $-CH=C(COO-iPr)-P(=O)(O-)(O-)$) | Calc. for $C_{18}H_{25}O_7P$:<br>C 56.25 H 6.57 P 8.06<br>found:<br>C 55.6 H 6.4 P 7.7<br>HPLC (m = 20; n = 60;<br>R = 98.27; t = 8.005) | 1 |
| 72 | (structure: phenyl with $H_3C-O-$ and $-O-CH_2-(CH_2)_4-CH_3$ substituents, connected to $-CH=C(C(=O)-O-iPr)-P(=O)(O-)(O-)$) | Calc. for $C_{21}H_{33}O_7P$:<br>C 58.87 H 7.78 P 7.23<br>found:<br>C 58.5 H 7.7 P 7.0<br>HPLC (m = 20; n = 60;<br>R = 96.67; t = 11.549) | 9 |
| 73 | (structure: phenyl with $H_2C(Ph)-O-$ and $-O-CH_3$ substituents, connected to $-CH=C(COO-iPr)-P(=O)(O-)(O-)$) | Calc. for $C_{22}H_{27}O_7P$:<br>C 60.83 H 6.28 P 7.13<br>found:<br>C 60.7 H 6.1 P 7.0<br>HPLC (m = 20; n = 60;<br>R = 96.38; t = 9.012) | 1 |
| 74 | (structure: phenyl with two $H_2C(Ph)-O-$ substituents, connected to $-CH=C(COO-iPr)-P(=O)(O-)(O-)$) | Calc. for $C_{30}H_{35}O_7P$:<br>C 66.90 H 6.54 P 5.75<br>found:<br>C 67.3 H 6.5 P 5.7<br>HPLC (m = 20; n = 60;<br>R = 96.61; t = 12.962) | 1 |
| 75 | (structure: 1,4-benzodioxane substituted with $-CH_2-CH(C\equiv N)-P(=O)(O-Et)(O-Et)$) | MS (DCI) m/z 326.2 (M + H⁺) | 6 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 76 | 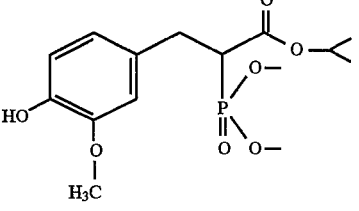 | MS (DCI) m/z 347.3 (M + H+) | 5 |
| 77 | 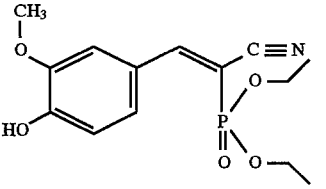 | Calc. for $C_{14}H_{18}NO_5P$: C 54.02 H 5.84 N 4.50 P 9.95 found: C 53.4 H 6.1 N 4.9 P 10.2 HPLC (m = 20; n = 60; R = 97.60; t = 9.004) | 1 |
| 78 | 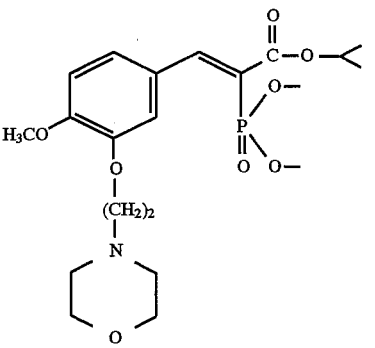 | MS (DCI) m/z 458.2 (M + H+) HPLC (m = 5; n = 30; R = 66.2; t = 4.108) | 9 |
| 79 | 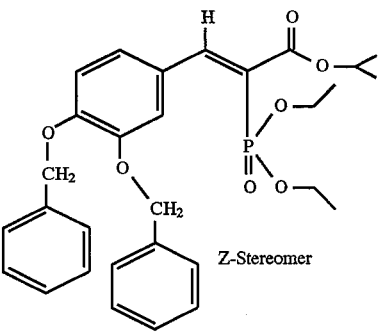 Z-Stereomer | Calc. for $C_{30}H_{35}O_7P$: C 66.90 H 6.54 P 5.57 found: C 66.3 H 6.3 P 5.5 HPLC (m = 50; n = 80; R = 90.34; t = 5.152) | 17 |
| 80 | 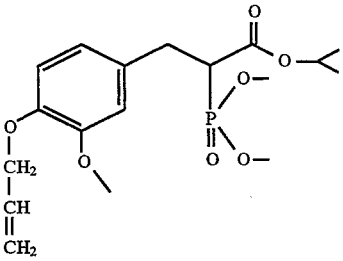 | MS (DCI) m/z 387.1 (M + H+) | 6 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|----|---------|---------------------|-------|
| 81 | | MS (DCI) m/z 375.1 (M + H$^+$) | 5 |
| 82 | | MS (DCI) m/z 467.4 (M + H$^+$)<br>HPLC (m = 30; n = 70;<br>R = 97.91; t = 10.96) | 1 |
| 83 | | Calc. for C$_{20}$H$_{27}$O$_7$P<br>C 58.53 H 6.64 P 7.54<br>found:<br>C 57.9 H 6.9 P 7.3<br>HPLC (m = 30; n = 70;<br>R = 98.75; t = 7.536) | 1 |
| 84 | | MS (DCI) m/z 460.4 (M + H$^+$) | 5 |
| 85 | | MS (DCI) m/z 437.3 (M + H$^+$) | 6 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 86 | | MS (DCI) m/z 437.3 (M + H$^+$) | 6 |
| 87 | | Calc. for $C_{16}H_{23}O_5P$<br>C 53.94 H 5.96 P 8.69<br>found:<br>C 53.8 H 5.9 P 8.5<br>HPLC (m = 40; n = 80;<br>R = 99.10; t = 2.121) | 1 |
| 88 | | MS (DCI) m/z 469.4 (M + H$^+$) | 5 |
| 89 | | MS (DCI) m/z 43.14 (M + H$^+$) | 5 |
| 90 | | MS (DCI) m/z 497.4 (M + H$^+$)<br>HPLC (m = 30; n = 70;<br>R = 91.057; t = 7.052) | 16 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 91 | | MS (DCI) m/z 459.4 (M + H⁺) HPLC (m = 40; n = 80; R = 88.97; t = 10.481) | 8 |
| 92 | | MS (DCI) m/z 413.0 (M + H⁺) | 6 |
| 93 | | MS (DCI) m/z 387.3 (M + H⁺) HPLC (m = 5; n = 50; R = 92.00; t = 11.417) | 18 |
| 94 | | MS (DCI) m/z 495.2 (M + H⁺) HPLC (m = 5; n = 50; R = 94.12; t = 11.346) | 19 |
| 95 | | MS (DCI) m/z 443.3 (M + H⁺) | 5 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 96 | | MS (DCI) m/z 497.2 (M + H$^+$) | 8 |
| 97 | | MS (DCI) m/z 436.1 (M + H$^+$)<br>HPLC (m = 5; n = 50;<br>R = 85.90; t = 5.625) | 8 |
| 98 | | MS (FAB) m/z 792.2 (M + H$^+$)<br>HPLC (m = 30; n = 70;<br>R = 76.1; t = 8.241) | 8 |
| 99 | | MS (DCI) m/z 389.3 (M + H$^+$) | 5 |
| 100 | | MS (DCI) m/z 327.2 (M + H$^+$)<br>Calc. for $C_{15}H_{19}O_6P$:<br>C 55.22 H 5.88 P 9.49<br>found:<br>C 5.8 H 6.2 P 9.3 | 1 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 101 | [structure] | MS (DEI) m/z 566<br>HPLC (m = 30; n = 70;<br>R = 96.32; t = 11.789) | 1 |
| 102 | [structure] | MS (DCI) m/z 528.2<br>HPLC (m = 30; n = 30;<br>R = 95.42; t = 7.008) | 8 |
| 103 | [structure] | MS (CEI) m/z 566<br>HPLC (m = 30; n = 70;<br>R = 90.93; t = 11.291 | 1 |
| 104 | [structure] | MS (DEI) m/z 460.41 | 5 |
| 105 | [structure] | MS (DEI) m/z 568 (M + H$^+$) | 6 |

TABLE 1-continued

The indicated preparation processes (right-hand column, abbreviation: proc.) for all the compounds
listed in Table 1 are analogous or identical to the processes for the examples specified in this column.

| No | Formula | Physical Properties | Proc. |
|---|---|---|---|
| 106 | | MS (FAB) m/z 430.2 (M + H⁺)<br>HPLC (m = 15; n = 70;<br>R = 92.437; t = 6.677) | 20 |
| 107 | | MS (FAB) m/z 317.1 (M + H⁺)<br>HPLC (m = 5; n = 50;<br>R = 96.736; t = 5.829) | 16 |
| 108 | | MS (DEI) m/z 312 | 1 |
| 109 | | MS (DEI) m/z 284 | 1 |
| 110 | | MS (FAB) m/z 430.2 (M + H⁺)<br>HPLC (m = 0; n = 70;<br>R = 84.02; t = 7.107) | 21 |
| 111 | | MS (FAB) m/z 475.1 (M + H⁺)<br>HPLC (m = 15; n = 70;<br>R = 96.58; t = 11.017) | 13 |

TABLE 1-continued

The indicated preparation processes (right-hand column, abbreviation: proc.) for all the compounds listed in Table 1 are analogous or identical to the processes for the examples specified in this column.

| No  | Formula | Physical Properties | Proc. |
|-----|---------|---------------------|-------|
| 112 | (structure, E) | MS (DEI) m/z 425<br>HPLC (m = 15; n = 70;<br>R = 93.00; t = 10.104) | 13 |
| 113 | (structure) | MS (FAB) m/z 354.2 (M + H$^+$)<br>HPLC (m = 0; n = 50;<br>R = 98.63; t = 11.558) | 1 |
| 114 | (structure) | MS (FAB) m/z 507.4 (M*)<br>HPLC (m = 20; n = 70;<br>R = 93.58; t = 10.252) | 6 |
| 115 | (structure, E) | MS (DEI) m/z 505<br>HPLC (m = 30; n = 70;<br>R = 99.28; t = 10.836) | 10 |
| 116 | (structure, Z) | MS (DEI) m/z 505<br>HPLC (m = 30; n = 70;<br>R = 94.11; t = 10.480) | 10 |
| 117 | (structure, (E)) | MS (DEI) m/z 424<br>HPLC (m = 10; n = 70;<br>R = 95.56; t = 4.996) | 8 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|---|---|---|---|
| 118 | (structure) | MS (DEI) m/z 355 | 1 |
| 119 | (structure) | MS (FAB) m/z 470.2 (M$^+$) | 6 |
| 120 | (structure) | MS (FAB) m/z 469.2 (M + H$^+$)<br>HPLC (m = 10; n = 70;<br>R = 78.03; t = 10.097) | 1 |
| 121 | (structure) | MS (DEI) m/z 314 | 5 |
| 122 | (structure) | MS (DEI) m/z 400<br>HPLC (m = 10, n = 50,<br>R = 96.58, t = 11.833) | 2 |

TABLE 1-continued
The indicated preparation processes (right-hand column, abbreviation: proc.) for all the compounds listed in Table 1 are analogous or identical to the processes for the examples specified in this column.
| No | Formula | Physical Properties | Proc. |
|---|---|---|---|
| 123 | 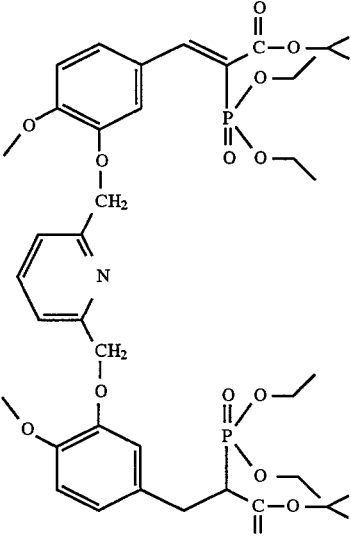<br>1944 JK 630-2 | MS (ESI) m/z 792.4 (M + H$^+$)<br>HPLC (m = 30; n = 70;<br>R = 93.54; t = 7.023) | 8 |
| 124 | 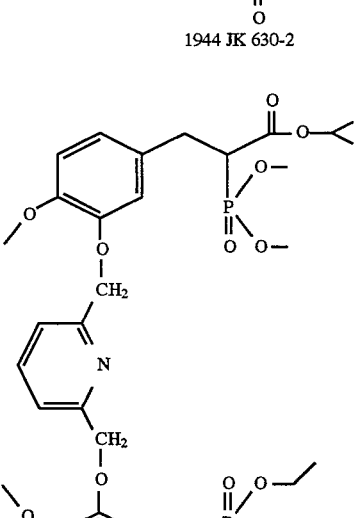<br>1935-KpO-224-1 | MS (ESI) m/z 796.4 (M + H$^+$) | 6 |

TABLE 1-continued
The indicated preparation processes (right-hand column, abbreviation: proc.) for all the compounds listed in Table 1 are analogous or identical to the processes for the examples specified in this column.
| No | Formula | Physical Properties | Proc. |
|---|---|---|---|
| 125 | 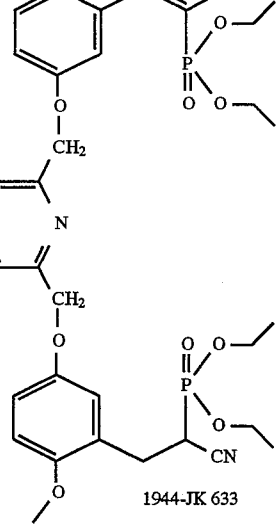 1944-JK 633 | MS (ESI) m/z 726.4 (M + H+) HPLC (m = 30; n = 70; R = 95.75; t = 7.959) | 8 |
| 126 | 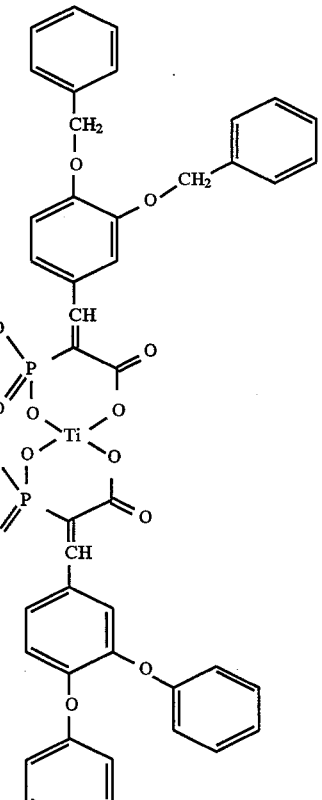 1935-KpO-138-3 | Calc. for $C_{48}H_{42}O_{14}P_2Ti$: C 60.52, H 4.45, Ti 5.03, P 6.50 found: C 59.3, H 5.1, Ti 5.30, P 6.5 HPLC (m = 30; n = 70; R = 85.94; t = 5.357) | 2 |

TABLE 1-continued

The indicated preparation processes (right-hand column, abbreviation: proc.) for all the compounds listed in Table 1 are analogous or identical to the processes for the examples specified in this column.

| No | Formula | Physical Properties | Proc. |
|----|---------|---------------------|-------|
| 127 |  | MS (DEI) m/z 474<br>HPLC (m = 30; n = 70;<br>R = 82.4; t = 2.702) | 8 |

PHARMACOLOGICAL TESTS

1. Efficacy in chondrolysis, test in chondrocyte culture

Cells: The hyaline cartilage was removed from the foot joints of freshly slaughtered cattle, the matrix was broken down enzymatically with pronase (Boehringer Mannheim) and collagenase (Sigma), and the chondrocytes were plated out in 1 percent low melting agarose in 24-well dishes at a cell density of 4×10' per well.

Medium: complete medium contains F12 HAM (Biochrom KG, Berlin) and 10% fetal calf serum (Boehringer Mannheim), the test substance was dissolved in medium, normally added at a concentration of 10—M and added anew at each change of the medium.

Test procedure: The treatment took place from the third to the tenth day of primary culture and, on day 9, 20 µCi/ml (7.4×10- Bq) of $Na_2{}^{35}SO_4$ were added to the medium for 24 h. The proteoglycans were extracted from the agarose layer with 8M guanidium chloride and in the presence of proteinase inhibitors (Sigma) with shaking at 4° C. for 24 hours. The supernatant after centrifugation was separated on a PD 10 ®Sephadex G 25 column into free and incorporated sulfate, whose activity was measured on aliquots in a a-scintillation counter.

Analysis: The parameter for matrix production by chondrocytes is the amount of synthesized proteoglycans measured as sulfate incorporation in disintegrations per minute (cpm). The mean was calculated for four wells in each group. This was divided by the mean for the control Dtreated with interleukin I (IL-I) and thus afforded a stimulation factor which was greater than 1 on stimulation of matrix synthesis, less than 1 on inhibition thereof by the effect of the substance, and equal to 1 when matrix synthesis was unaltered. The standard used was diacerein which is used as an osteoarthritis remedy in Italy under the proprietary name Artrodar.

Results: The results are listed in Table 2.

TABLE 2

Effect on IL-I-induced chondrolysis in agarose culture

| Example No. | Proteoglycan synthesis stimulation factor |
|-------------|-------------------------------------------|
| Standard (diacerein) | 1.1 |
| 10 | 3.5 |
| 12 | 4.1 |
| 13 | 3.3 |
| 14 | 3.8 |
| 15 | 3.4 |
| 21 | 1.3 |
| 24 | 1.6 |
| 25 | 2.1 |
| 26 | 2.1 |
| 27 | 1.9 |
| 28 | 3.0 |
| 29 | 3.4 |
| 35 | 1.3 |
| 39 | 1.2 |
| 40 | 1.2 |
| 41 | 1.2 |
| 47 | 2.4 |
| 49 | 1.4 |
| 50 | 1.4 |
| 51 | 1.3 |
| 52 | 1.4 |
| 53 | 2.1 |
| 55 | 1.2 |
| 60 | 2.5 |
| 61 | 2.4 |
| 62 | 2.5 |
| 63 | 2.5 |
| 87 | 1.4 |

2. Inhibition of matrix metalloproteases (NMP)

The compounds according to the invention show-marked inhibitory effects on proteolytic enzymes, the so-called matrix metalloproteases. This is of great importance because these enzymes, which are known per se to the skilled worker, are crucially involved in the proteolytic breakdown of intact cartilage matrix.

Cell culture: rabbit synoviocytes (HIG-82; ATCC, Rockville, Md., USA) were cultivated in nutrient medium F12 HAM (Sigma, Deisenhofen, Germany, Catalog No. N-6760) with 10% fetal calf serum (Sigma, Deisenhofen, Germany, Catalog No. F-2442), together with penicillin 100 U/ml and streptomycin 100 µg/ml. After confluent cell growth, the MMP expression was induced in the serum-free 3F12 HAM medium by adding 0.3 μmol/l phorbol 12-myristate 13-acetate. The supernatant was removed after incubating at 37° C. for 20 hours.

Activation of the MMP: The supernatant was activated with trypsin (5 μg/ml). After 15 minutes at 37° C., the activation was stopped by adding 1 mmol/l phenylmethylsulfonyl fluoride (PMSF) and incubating for a further 10 minutes. The total volume of the mixture was 210 μl.

Measurement of the MMP activity (C. G. Knight et al.: FEBS Lett. 296: 263, 1992): 20 μl of the abovementioned supernatant were diluted 1:10 and mixed with 240 μl of buffer (0.1M Tris/HCl pH 7.5; 0.1M NaCl; 0.01M $CaCl_2$; 0.05% Brij). The test substance was added in the stated concentration (see table). After incubation for 15 minutes, the reaction was started by adding 20 μmol/l fluorescent substrate ((7-methoxycoumarin-4-yl) acetyl Pro-Leu-Gly-Leu-[3-(2,4-dinitrophenyl)-L-2,3-diamino-propionyl]-Ala-Arg-$NH_2$ (Bathem, Heidelberg, Germany, Catalog No. M-1895)). The reaction was stopped after 30 minutes by adding 10 mmol/l EDTA. The total-volume of the mixture was 320 μl. The parameters measured were the fluorescence intensities at $\lambda_{em}$: 328 nm and $\lambda_{ex}$: 393 nm. In order to take account of the possible intrinsic fluorescence of the test substances, the fluorescence intensities from parallel measurements without substrate were subtracted from the measurements with substrate. All the steps took place at 20° C. In the control experiment without inhibitor, the fluorescence corresponding to 0% inhibition was employed, while complete quenching of the fluorescence meant 100% inhibition. Results: The results are listed in Table 3.

TABLE 3

| Inhibition of MMP | | |
|---|---|---|
| Example | Inhibition (%) | Concentration (μM) |
| 14 | 50 | 100 |
| 14 | 19 | 30 |
| 15 | 26 | 100 |
| 15 | 4 | 30 |
| 21 | 51 | 100 |
| 21 | 19 | 30 |
| 26 | 51 | 100 |
| 25 | 24 | 30 |
| 26 | 15 | 10 |
| 27 | 48 | 100 |
| 27 | 24 | 30 |
| 28 | 9 | 100 |
| 31 | 35 | 100 |
| 31 | 12 | 30 |
| 31 | 8 | 10 |
| 32 | 52 | 100 |
| 32 | 22 | 30 |
| 32 | 12 | 10 |
| 35 | 52 | 100 |
| 35 | 21 | 30 |
| 39 | 47 | 100 |
| 39 | 19 | 30 |
| 39 | 16 | 10 |
| 40 | 13 | 100 |
| 47 | 55 | 100 |
| 47 | 24 | 30 |
| 47 | 13 | 10 |
| 48 | 26 | 100 |
| 48 | 9 | 30 |
| 48 | 7 | 10 |
| 49 | 28 | 100 |
| 49 | 8 | 30 |
| 50 | 14 | 100 |
| 51 | 14 | 100 |

3. Inhibition of microsomal lipid peroxidation

Oxidative breakdown processes are also involved to a considerable extent in the unwanted breakdown of cartilage matrix. The compounds according to the invention show a strong inhibitory effect on biological oxidation processes and are therefore particularly suitable for inhibiting oxidative cartilage breakdown.

Obtaining rat liver microsomes: All steps were carried out at 0° C. The liver from a rat was thoroughly rinsed with 0.9% NaCl solution to remove all the hemoglobin. The liver wascut into pieces and then treated in a Potter in 10 mM Tris/HCl pH 7.4; 250 mM sucrose (10 ml of buffer/g of liver). The first centrifugation was at 600 x g for 55 minutes to remove cell detritus. The supernatant was then centrifuged at 12000 x g for 10 minutes and was adjusted with solid $CaCl_2$ (117.6 mg/100 ml) to a concentration of 8 mM. A microsome pellet was obtained by centrifugation at 25000 x g (15 minutes). This pellet was ohomogenized in the same volume of buffer (10 mM Tris/BCI pH 7.4; 150 mMKCl) and again centrifuged at 25000 x g for 15 minutes.

Peroxidation by rat liver microsomes: A test mixture consisted of 20 μl of microsomes (100 mg/ml), see above, dissolved in a buffer (250 mM Tris/HCI pB 6.6; 750 mMKCl), 10 iL1 of 50 mM $MgCl_2$, 10 μl of 200 mM isocitric acid, 10 μl of 4 mM NADP (3.028 mg/ml in water), 10 μl of 25 mM niacinamide, 10 μl of isocitrate dehydrogenase (Boehringer, diluted 1:100) and 20 μl of water or test substance. The reaction was started with 10 μl of 0.25 mM $FeSO_4$. Incubation lasted 10 minutes and took place at 37° C. It was stopped with 500 μl of ice-cold 20 percent trichloroacetic acid. The malonaldehyde which was formed was converted by adding 500 μl of 0.67 percent thiobarbituric acid and incubating at 90° C. for 30 min into a pink-colored compound which was measured in a photometer at 532 nm. The extinction in the control mixture without test substance was set at 0% inhibition, while complete disappearance of the signal meant 100% inhibition. Results: The results are listed in Table 4.

TABLE 4

| Microsomal lipid peroxidation | |
|---|---|
| Example | $IC_{50}$ (μmol/l) |
| 47 | 2.10 |

4. Release of interleukins (for example IL-1β) from human mononuclear cells

The compounds according to the invention have a strong inhibitory effect on the release of interleukins from human cells. This is of great pharmacological importance because interleukins may induce unwanted breakdown of cartilage matrix.

Obtaining mononuclear cells from human blood: 10 ml of human blood stabilized with 1 ml of 3.8 percent sodium citrate solution were diluted with 10 ml of PM16 (Serra, Heidelberg), and an underlayer of 15 ml of Lymphoprep (Dr. Molter GmbH, Heidelberg) was introduced. The samples were centrifuged at 400 x g (Minifuge 2 Heraeus, Osterode) at room temperature for 40 minutes. The mononuclear cells were visible as a white ring at the Lymphoprep/plasma boundary. This ring was cautiously removed with a syringe, diluted with the same volume of PM16 and centrifuged at 400 x g for 10 minutes. The precipitate was washed with ~10 ml of RPMI1640 (+300 mg/I L-glutamine, Gibco, Eggenstein). After the cells had been suspended in ~1 ml of RPMI1640 (+300 mg/I L-glutamine, +25 mM HEPES, +100 μg/ml streptomycin, +100 μg/ml penicillin), the cell density was determined with a JT Coulter Counter (Coulter Diagnostics) and adjusted to $5.10^6$/ml. 90% of the resulting cells were lymphocytes and 10% were monocytes.

Inhibition of release of interleukin-1β: 230 μl of mononuclear cells were incubated with 10 μl of test substance (10 μM in dimethyl sulfoxide (DMSO)/water=1/10) and 10 μl of a lipopolysaccharide solution (500 μg dissolved in 1 ml of DMSO and diluted 1/10 with water before starting the test, from Salmonella abortus equi, (Sigma, Deisenhofen) at 37° C., 5% $CO_2$ for 20 to 22 hours. The samples were cooled to 0° C. in an ice bath and centrifuged in a Sigma centrifuge (2 minutes; 2000 revolutions per minute (rpm)). Aliquots of the supernatant were determined using a commercially available ELISA 5(Biermann, Bad Nauheim). Results: The results are listed in Table 5.

TABLE 5

Inhibition of interleukin release

| Example | % inhibition |
| --- | --- |
| 26 | 59 |
| 27 | 99 |
| 31 | 97 |
| 32 | 80 |
| 35 | 83 |
| 36 | 15 |
| 39 | 63 |
| 41 | 11 |
| 42 | 77 |
| 47 | 80 |
| 63 | 92 |

All active substances were tested at a concentration of 10 μmol/l. IL-1β release was tested in each case.

5. Efficacy as antagonist of the contraction of the isolated guinea pig trachea

The compounds according to the invention are used as antagonists of the contraction of various parts of organs, in this case the isolated guinea pig trachea. The agonists used were KCl, $PGF_{2\alpha}$, calcium ionophore A23187 and substance P:

a) KCl

Products with a non-specific effect generally show a spasmolytic effect with respect to all agonists. KCI is representative here of non-specific, receptor-independent contraction because KCl-induced contractions are produced predominantly physically, that is to say by increasing the K+ concentration in the outside medium, and change the resting potential of the cell.

b) PGF2a

PGF2a displays its contractile effect via its own receptors. Inhibition of contractions induced by this cyclooxygenase product is possible only by competitive antagonism at the receptor or of the downstream signal pathway.

c) Calcium ionophore A23187 (Calbiochem, Bad Soden) brings about, due to increased uptake of calcium ions, an activation of all calcium-dependent signal cascades in the cell. Lipoxygenase inhibitors in particular, and substances with antiinflammatory activity in general, showed effects in this model.

d) Substance p

Substance P as a transmitter between the immune system and nervous system showed a contractile effect on smooth muscles. Antagonism is possible on the one hand by specific receptor antagonists, and on the other hand by inhibition of the downstream signal pathway. Products which directly or indirectly increase the intracellular concentration of cyclic nucleotides showed spasmolytic properties in this case in particular.

Preparation of the parts of the organs and test procedure:

The guinea pigs were sacrificed by lethal anesthesia with laughing gas. The trachea was dissected out over its entire length and cut into 15 individual cartilage rings. In each case five rings were connected together to form a chain and fixed in an organ bath under a preload of 3 g. After an equilibration period of 45 minutes, a contraction was induced with the agonist. Cumulative addition of the antagonist (test product) took place at the plateau 5 of the maximum. Evaluation took place as % change in strength based on the maximum contraction. The test was carried out at 37° C., and the physiological nutrient solution used was a modified Krebs-Henseleit solution through which 95% by volume 02 and 5% by volume $CO_2$ was bubbled.

Test animals: Albino guinea pigs (102), weight: 200 to 300 g, male or female

Composition of the organ bath (nutrient solution):

| Modified Krebs-Henseleit solution and calcium ionophore | | for the agonists KCl, $PGF_{2a}$ for the agonist SP |
| --- | --- | --- |
| NaCl | 6.9 g | NaCl |
| $KH_2PO_4$ | 0.14 g | $KH_2PO_4$ |
| $NaHCO_3$ | 2.1 g | $NaHCO_3$ |
| glucose | 2.0 g | glucose |
| KCl | 0.35 g | KCl |
| $CaCl_2$ | 0.28 g | $CaCl_2$ |
| $MgSO_4$ | 0.14 g | to 1 l double-distilled water |

Vehicle: Double-distilled water, ethanol or isopropanol; Administration: into the organ bath Number of administrations: cumulative, single doses for SP Results: The compounds according to the invention showed an antagonistic effect with respect to KCl, the prostaglandin $PGF_{2a}$, calcium ionophore (A 23187) and substance P. The results are listed in Table 6.

TABLE 6

Anticontractile effect (trachea)

| Example | KCl | $PGF_{2\alpha}$ | Ca ionophore | Substance P |
| --- | --- | --- | --- | --- |
| 11 | >10 | >10 | | 10–30 |
| 30 | >10 | 6–10 | 3–6 | 10–30 |
| 34 | >10 | >10 | | 1–10 |
| 37 | approx. 10 | approx. 3 | approx. 1 | approx. 3 |
| 38 | >10 | 1–3 | approx. 3 | 3–10 |
| 44 | >10 | approx. 6 | | 10–30 |
| 52 | >10 | >10 | 6–10 | |

The unit for all the numerical values is μg/ml, and they relate to the concentration range of tested compound according to the invention (see example numbers in Table 1) needed to bring about a dilatation corresponding to the $ED_{50}$ range.

6. Efficacy as antagonist of the contraction of iso lated strips of guinea pig lung The test was based on the same principle as the test indicated in Pharmacological Test 5; however, strips of lung were used in this case.

Preparation of the parts of organs and test procedure:

The guinea pig was sacrificed under anesthesia with laughing gas. The entire lung tract was cut out starting from the trachea. The lobes of the lungs were cut in circular fashion to produce strips about 3 mm wide. The strips of the upper lobes were divided up in order to obtain a total of six strips of approximately equal size. The strips were suspended in the organ baths under a preload of 4 g. Modified Krebs-Henseleit solutions were used as nutrient solution. When platelet activating factor (PAF) was used as agonist, the composition of this solution corresponded to that for the agonist SP in Pharmacological Test 5; a Krebs-Henseleit solution as in the case of the agonist KCl (Pharm. Test 5) was used for the agonist $LTD_4$. 95% by volume $O_2$, 5% by volume $CO_2$ was bubbled through the bath, and the bath temperature was 37° C. The test is carried out by a therapeutic/cumulative method with dose levels of 1, 3, 6 and 10 µg/ml.

The test animals, organ bath, vehicle, mode of administration corresponded to that stated for Pharmacological Test 5.

Results: The compounds according to the invention showed an antagonistic effect with respect to leukotriene $D_4$ ($LTD_4$) and the membrane lipid platelet activating factor. The results are listed in Table 7.

TABLE 7

| | Anticontractile effect (lung) | |
|---|---|---|
| Example | $LTD_4$ | PAF |
| 1 | >10 | 1–3 |
| 4 | 3–6 | 1–3 |
| 9 | 1–3 | 1–3 |
| 11 | | 6–10 |
| 30 | approx. 10 | 1–3 |
| 37 | 0.1–0.3 | 1–3 |
| 38 | approx. 1 | <0.1 |
| 39 | approx. 10 | |
| 40 | >10 | 1–3 |
| 41 | >10 | 1–3 |
| 42 | >10 | 3–6 |
| 46 | approx. 10 | 1–3 |
| 56 | 3–6 | 1–3 |
| 61 | >10 | approx. 3 |
| 70 | approx. 6 | |

The unit for all the numerical values is µg/ml, and they relate to the concentration range of tested compound oaccording to the invention (see example numbers in Table 1) needed to bring about a contraction corresponding to the $IC_{50}$ value.

7. Adjuvant arthritis

The investigations were carried out as described in EP 50 42 740. After intraperitoneal administration of 12.6 mg of compound 38 per kg of Wistar-Lewis rats twice a day for 18 days there was 98% inhibition of the increase in the paw volume compared with an untreated control group.

8. Release of tumor necrosis factor oL (TNFa) and substance P from RAW 264.7 cells Culture medium: DMEM+10% FCS+penicillin/streptomycin (50 U/SO µg/ml)
Culture conditions: 37° C., 10% $CO_2$
Culture dishes: 24-well dishes
In each case $10^6$ cells/ml/well were incubated for 24 hours (h)

Addition of 10 µl of test substance (=100 µM in the test, dissolved in double-distilled water)
Incubation for 1 h
Addition of 50 µl of lipopolysaccharide (LPS) from E. coli (=10 pg/ml in the test, dissolved in culture medium)
Incubation for 2.5 h and 24 h Tumor necrosis factor α was determined using a Factortest X mouse TNFα ELISA kit from Genzyme (R(lsselsheim, Geromany), Order no. 80-2802-00.

Compound 37 showed 55% inhibition of TNFcL formation compared with an untreated control after incubation for 2.5 hours (h); Compound 38 showed 16% inhibition after incubation for 4 h.

Release of substance P took place as described for TNFα, but the cells were stimulated by 50 ng of LPS for 4 hours. Substance P was determined using a substance P RIA test kit from Peninsula Laboratories (Belmont, USA) Test no. RIK-7451.

The untreated cells produced 20 pg/ml substance P, while Compounds 37 and 38 inhibited substance P production by 100%.

9. Inhibition of phosphodiesterase III activity

The test was carried out with the phosphodiesterase of Boehringer Mannheim (Mannheim, Germany), Order no. 108 243 by the method of T. SAEKI, I. SAITO, Biochem. Pharm. 46, No. 5, (1986), pages 833–839.

100 µM of Compound 37 brought about a 39% inhibition of enzyme activity in the test.

What is claimed is:

1. A compound selected from at least one of a compound of the formula (I)

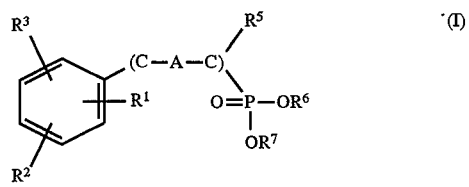

a physiologically tolerated salt thereof, and a stereoisomer thereof, where at least two of the radicals $R^1$, $R^2$ and $R^3$ are present and are, independently of one another, selected from:

1) OH,
2) ($C_1$–$C_{12}$)-alkoxy,
3) —O—($C_1$–$C_{12}$)-alkyl-COOH,
4) —O—($C_1$–$C_{12}$)-alkyl-C(O)—O—($C_1$–$C_{12}$)-alkyl,
5) ($C_3$–$C_{12}$)-cycloalkoxy,
6) ($C_3$–$C_6$)-alkenyloxy,
7) ($C_5$–$C_7$)-cycloalkyl-($C_1$–$C_3$)-alkoxy,
8) heteroaryl-($C_1$–$C_3$)-alkoxy, where the hetero atoms are selected from N, S and O,
9) heterocycloalkyl-($C_1$–$C_3$)-alkoxy where the heteroatoms are selected from N, S and O, the heterocyclo alkyl radical is unsubstituted or substituted once to three times by ($C_1$–$C_3$)-alkyl, and the heterocycloalkyl group has five or six members,
10) phenyl-($C_1$–$C_3$)-alkoxy,
11) benzyloxy substituted once to three times by halomethyl or ($C_1$–$C_3$)-alkoxy,
12) phenoxy substituted once to three times by ($C_1$–$C_3$)-alkoxy,
13) two of the radicals $R^1$, $R^2$ or $R^3$ which are substituents on two directly adjacent carbon atoms of the aromatic ring together form a methylenedioxy or ethylenedioxy radical on the aromatic ring, 14) a radical of the formula II, III or IV

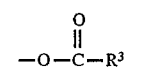  (II)

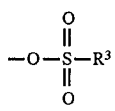  (III)

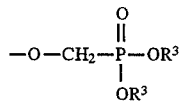  (IV)

where $R^8$ is $(C_1-C_4)$-alkyl, or hydrogen, 15) a group of the formula V

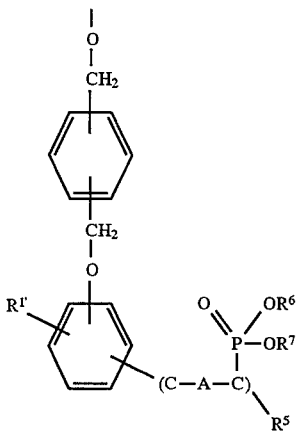  (V)

$R^{1'}$ is defined as for $R^1$ from 1) to 12), and (C-A-C), $R^5$, $R^{'}$ and $R^7$ are as defined below, or 16) $R^1$ and $R^7$ are a covalent bond and thus form a compound of the formula Ia

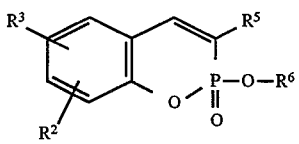  (Ia)

where $R^2$ and $R^3$ are as defined above and $R^5$ and $R^6$ are as defined below, or 17) $R^1$ and $R^5$ are a covalent bond and thus form a compound of the formula Ib

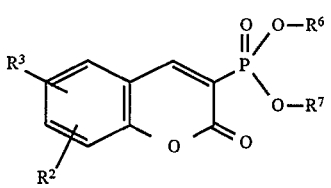  (Ib)

where $R^2$ and $R^3$ are as defined above and $R^6$ and $R^7$ are as defined below, and $R^5$ is
1) CN,
2) $CH_2NHR^9$ where $R^9$ is hydrogen atom or —$(C_1-C_3)$-alkyl, or 3) a radical of the formula VI

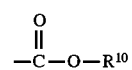  (VI)

where
$R^{10}$ is
1) hydrogen,
2) $(C_1-C_6)$-alkyl, unsubstituted or substituted once to four times by —COOH, —C(O)—O—$(C_1-C_3)$-alkyl or

where R is hydrogen, $(C_1-C_3)$-alkyl or forms, together with the nitrogen atom to which it is bonded, a morpholine ring, or 3) trialkylsilyl, $R^6$ and $R^7$ are, independently of one another,
1) hydrogen or
2) $(C_1-C_6)$-alkyl, (C-A-C ) is
1) (CH=CH—CH=C),
2) ($CH_2$—$CH_2$—$CH_2$—CH),
3) ($CH_2$—$CH_2$—CH),
4) (—$CH_2$—C) or
5) (—CH=C)

with the proviso that when the radical $R^5$ is a CN group, not more than one of the radicals $R^1$, $R^2$ or $R^3$ is a hydroxyl radical, or when the radical $R^{10}$ is a hydrogen atom, none of othe radicals $R^1$, $R^2$ or $R^3$ is a hydroxyl radical, or when the radical $R^{10}$ is methyl, ethyl or t-butyl, the radicals $R^1$, $R^2$ or $R^3$ are not methoxy, and the compounds

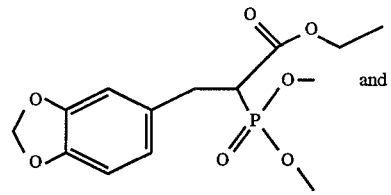 and

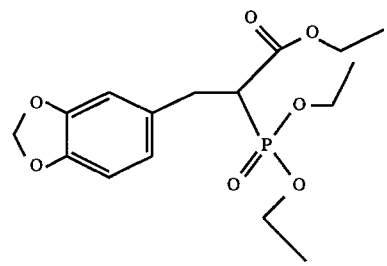

are excepted.

2. A compound of the formula I as claimed in claim 1, where at least two of the radicals $R^1$, $R^2$ and $R^3$ are present and are selected from, independently of one another,
1) OH
2) $(C_1-C_6)$-alkoxy,
3) —O—$(C_1-C_6)$-alkyl-COOH,
4) —O—$(C_1-C_6)$-alkyl-C(O)—O—$(C_1-C_6)$-alkyl,
5) $(C_5-C_7)$-cycloalkoxy, 6) $(C_3-C_6)$-alkenyloxy, 8) heteroaryl-$(C_1-C_2)$-alkoxy, where the hetero-atoms are selected from N and O, 9) heterocycloalkyl-$(C_1-C_2)$-alkoxy where the heteroatoms are selected from N and O, the heterocycloalkyl radical is unsubstituted or substituted once to three times by $(C_1-C_3)$-alkyl, and the heterocycloalkyl group has five or six members, 10) phenyl-$(C_1-C_2)$-alkoxy, 11) benzyloxy substituted once to three times by halomethyl or $(C_1-C_3)$-alkoxy, 12) phenoxy substituted once to three times by $(C_1-C_3)$-alkoxy, 13) two of the radicals $R^1$, $R^2$ and $R^3$ are both a group having the formula (II)

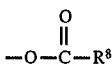  (II)

where $R^8$ is $(C_1-C_4)$-alkyl, and
$R^5$ is selected from
1) CN,
2) $CH_2NHR^9$ where $R^9$ is hydrogen or —C(O)—$(C_1-C_3)$-alkyl, and
3) a radical of the formula VI

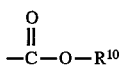  (VI)

where $R^{10}$ is selected from
1) hydrogen,
2) $(C_1-C_6)$-alkyl, unsubstituted or substituted once by a group selected from
   (i)-COOH,
   (ii)—C(O)—$(C_1-C_3)$-alkyl and
   (iii)

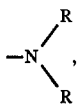

where R is $(C_1-C_3)$-alkyl, and
3) trialkylsilyl, $R^6$ and $R^7$ are, independently of one another, hydrogen or $(C_1-C_4)$-alkyl, and (C-A-C) is 1) (—$CH_2$—CH) or 2) (—CH=C).

3. A compound of the formula I as claimed in claim 1 where $R^1$ is methoxy, $R^2$ is methoxy or benzyloxy, $R^3$ is methoxy or benzyloxy, and $R^5$ is selected from
1) CN,
2) $CH_2NHR^9$, where $R^9$ is hydrogen or —C(O)—$(C_1-C_3)$-alkyl and
3) a radical of the formula VI, where $R^{10}$ is selected from
   i) hydrogen and
   ii) $(C_1-C_4)$-alkyl substituted by
      (1) —COOH, or

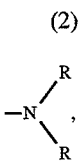  (2)

where R is selected from hydrogen and $(C_1-C_3)$-alkyl, $R^6$ and $R^7$ are, independently of one another, hydrogen or $(C_1-C_4)$-alkyl, and (C-A-C) is a (—CH=C) radical.

4. A compound of the formula I as claimed in claim 1 where $R^1$ is hydrogen, $R^2$ and $R^3$ are both methoxy, and $R^5$ is a group of the formula VI where $R^{10}$ is hydrogen or isopropyl, $R^6$ and $R^7$ are both ethyl or methyl, and (C-A-C) is a (—$CH_2$—CH) radical.

5. A compound of the formula I as claimed in claim 1, where $R^1$ is hydrogen, $R^2$ and $R^3$ are both benzyloxy, and $R^5$ is a group of the formula VI where $R^{10}$ is hydrogen or isopropyl, $R^7$ and $R^7$ are methyl or ethyl, and (C-A-C) is a (—CH=C) radical.

6. A process for preparing the compound of the formula I as claimed in claim 1, said process comprising a) reacting a compound of the formula VII

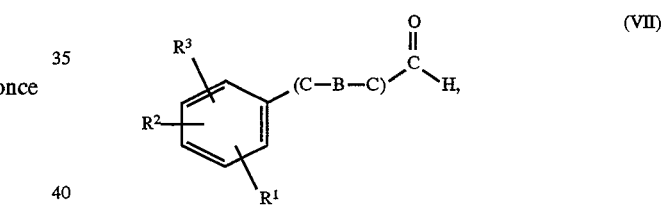  (VII)

where $R^1$, $R^2$ and $R^3$ are as defined in claim 1, and (C-B-C) is selected from a covalent bond, (—CH=CH—), (—$CH_2$—CH2—$CH_2$), (—$CH_2$—$CH_2$) or (—$CH_2$—), with a compound of the formula VIII or a salt thereof,

  (VIII)

where $R^5$, $R^6$ and $R^7$ are defined as in claim 1, in the presence of tetrahydrofuran and titanium tetrachloride, or in the presence of tetrahydrofuran and an orthotitanic triester of the formula IX (IX)  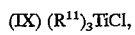, where $R^{11}$ is —O—$(C_1-C_6)$-alkyl, and b) fractionating a compound of the formula I which has been prepared by process a) and which is present in enantiomeric or stereoisomeric form, separating the diastereomers obtained, and eliminating the chiral auxiliary group, thus producing the pure enantiomers.

7. The process of claim 6, further comprising the step of isolating the compound of the formula I which has been prepared by step b) in free form or, if acidic or basic groups are present, converting it into physiologically tolerated crystalline salts.

8. The process of claim 6, wherein the fractionating step is carried out by salt formation with enantiomerically pure acids or bases.

9. The process of claim 6, wherein the fractionating step is carried out by chromatography on chiral stationary phases.

10. The process of claim 6, wherein the fractionating step is carried out by derivatization using chiral enantiomerically pure compounds.

11. The process of claim 6, wherein said stereoisomers are fractionated by chromatography.

12. A process for preparing the compound of the formula I as claimed in claim 1, said process comprising a) reacting a compound of the formula VII

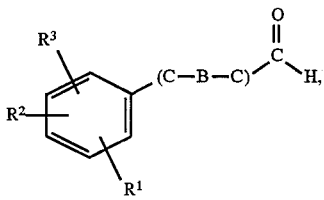

where $R^1$, $R^2$ and $R^3$ are as defined in claim 1, and (C-B-C) is selected from a covalent bond, (—CH=CH—), (—CH$_2$—CH$_2$—CH$_2$), (—CH$_2$—CH$_2$) or (—CH$_2$—), with a compound of the formula VIII or a salt thereof,

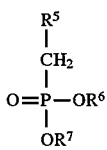

where $R^5$, $R^6$ and $R^7$ are defined as in claim 1, in the presence of tetrahydrofuran and titanium tetrachloride, or in the presence of tetrahydrofuran and an orthotitanic triester of the formula IX (IX) $(R^{11})_3$TiCl, where $R^{11}$ is —O—(C$_1$-C$_6$)-alkyl, and b) hydrolyzing a compound of the formula I which has been prepared as in a), where at least one of $R^1$, $R^2$ or $R^3$ is a radical of the formula II or III, to the corresponding phenol.

13. The process according to claim 12, further comprising the step of carrying out the reaction of process b) in the presence of sodium bicarbonate.

14. The process of claim 12, further comprising the step of isolating the compound of the formula I which has been prepared by process b) in free form or, if acidic or basic groups are present, converting it into physiologically tolerated crystalline salts.

15. A process for preparing the compound of the formula I as claimed in claim 1, said process comprising a) reacting a compound of the formula VII

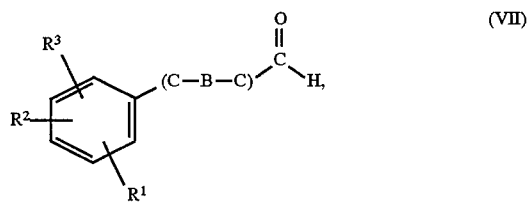

where $R^1$, $R^2$ and $R^3$ are as defined in claim 1, and (C-B-C) is selected from a covalent bond, (—CH=CH—), (—CH$_2$—CH$_2$—CH$_2$), (—CH$_2$—CH$_2$) and (—CH$_2$—), with a compound of the formula VIII or a salt thereof,

where $R^5$, $R^6$ and $R^7$ are defined as in claim 1, in the presence of tetrahydrofuran and titanium tetrachloride, or in the presence of tetrahydrofuran and an orthotitanic triester of the formula IX (IX) $(R^{11})_3$TiCl, where $R^{11}$ is —O—(C$_1$-C$_6$)-alkyl, and b) hydrolyzing a compound of the formula I which has been prepared as in a), wherein $R^5$ is a radical of the formula VI and at least one $R^1$, $R^2$ or $R^3$ is a radical —O—(C$_1$-C$_{12}$)-alkyl-C(O)—O—(C$_1$-C$_{12}$)-alkyl, to the carboxylic acid.

16. The process of claim 15, further comprising the step of carrying out the reaction of process b) in the presence of an ethanolic potassium hydroxide solution or a hydrochloric acid solution.

17. The process of claim 15, further comprising the step of isolating the compound of the formula I which has been prepared by process b) in free form or, if acidic or basic groups are present, converting it into physiologically tolerated crystalline salts.

18. A process for preparing the compound of the formula I as claimed in claim 1, said process comprising a) reacting a compound of the formula VII

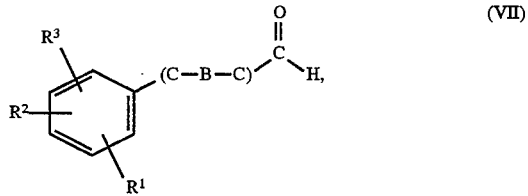

where $R^1$, $R^2$ and $R^3$, are as defined in claim 1, and (C-B-C) is selected from a covalent bond, (—CH=CH—),(—CH$_2$—CH$_2$—CH$_2$), (—CH$_2$—CH$_2$) and (—CH$_2$—), with a compound of the formula VIII or a salt thereof

where $R^5$, $R^6$ and $R^7$ are defined as in claim 1, in the presence of tetrahydrofuran and titanium tetrachloride, or in the presence of tetrahydrofuran and an orthotitanic triester of the formula IX

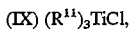

where $R^{11}$ is —O—$(C_1$–$C_6)$-alkyl, and b) hydrogenating a compound of the formula I which has been prepared as in a) and contains one or two double bonds with i) hydrogen and a Pd/C or Raney nickel catalyst or ii) sodium borohydride.

19. The process of claim 18, further comprising the step of isolating the compound of the formula I which has been prepared by process b) in free form or, if acidic or basic groups are present, converting it into physiologically tolerated crystalline salts.

20. A process for preparing the compound of the formula I as claimed in claim 1, said process comprising a) reacting a compound of the formula VII

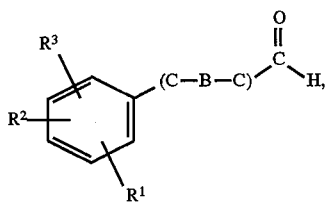

where $R^1$, $R^2$ and $R^3$ are as defined in claim 1, and (C-B-C) is selected from a covalent bond, (—CH=CH—), (—CH$_2$—CH$_2$—CH$_2$—), (—CH$_2$—CH$_2$) and (—CH$_2$—), with a compound of the formula VIII or a salt thereof,

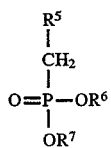

where $R^5$, $R^6$ and $R^7$, are defined as in claim 1, in the presence of tetrahydrofuran and titanium tetrachloride or in the presence of tetrahydrofuran and an orthotitanic triester of the formula IX

where $R^{11}$ is —O—$(C_1$–$C_6)$-alkyl, and b) hydrolyzing a monoalkyl or dialkyl phosphonate of the formula I which has been prepared as in a) to the phosphonic monoester or to the phosphonic acid, carrying out the cleavage of the phosphonic ester in the presence of bromotrimethylsilane in dichloromethane.

21. The process of claim 20, further comprising the step of isolating the compound of the formula I which has been prepared by process b) in free form or, if acidic or basic groups are present, converting it into physiologically tolerated crystalline salts.

22. A process for preparing the compound of the formula I as claimed in claim 1, said process comprising a) reacting a compound of the formula VII

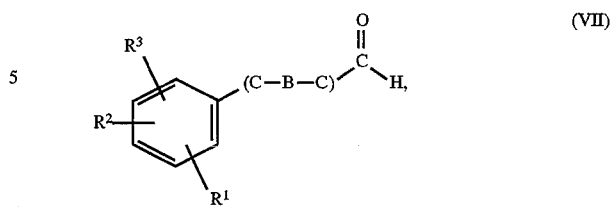

where $R^1$, $R^2$ and $R^3$ are as defined in claim 1, and (C-B-C) is selected from a covalent bond, (—CH=CB—), (—CH$_2$—CH$_2$—CH$_2$), (—CH$_2$—CH$_2$) and (—CH$_2$—), with a compound of the formula VIII or a salt thereof,

where $R^5$, $R^6$ and $R^7$ are defined as in claim 1, in the presence of tetrahydrofuran and titanium tetrachloride, or in the presence of tetrahydrofuran and an orthotitanic triester of the formula IX

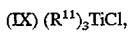

where $R^{11}$ is —O—$(C_1$–$C_6)$-alkyl, and b) isolating the compound of the formula I which has been prepared by process a) in free form or, if acidic or basic groups are present, converting it into physiologically tolerated crystalline salts.

23. A process for preparing the compound of the formula I as claimed in claim 1, said process comprising reacting a compound of the formula I where at least one of the radicals $R^1$, $R^2$ or $R^3$ is a hydroxyl radical with a compound of the formula XI

where X is halogen or optionally substituted phenylsulfonyloxy, and $R^{13}$ is selected from
1) OH
2) $(C_1$–$CH_{12})$-alkoxy,
3) —O—$(C_1$–$C_{12})$-alkyl-COOH,
4) —O—$(C_1$–$CH_{12})$-alkyl-C(O)—O—$(C_1$–$C_{12})$-alkyl,
5) $(C_3$–$C_{12})$-cycloalkoxy,
6) $(C_3$–$C_6)$-alkenyloxy,
7) $(C_5$–$C_7)$-cycloalkyl-$(C_1$–$C_3)$-alkoxy,
8) heteroaryl-$(C_1$–$C_2)$-alkoxy, where the heteroatoms are selected from N, S and O,
9) heterocycloalkyl-$(C_1$–$C_3)$-alkoxy where the heteroatoms are selected from N, S, and O, the heterocycloalkyl radical is unsubstituted or substituted once to three times by $(C_1$–$C_3)$-alkyl, and the heterocycloalkyl group has five or six members,
10) phenyl-$(C_1$–$C_2)$-alkoxy,
11) benzyloxy substituted once to three times by halomethyl or $(C_1$–$C_3)$-alkoxy,
12) phenoxy substituted once to three times by $(C_1$–$C_3)$-alkoxy, after treatment with sodium hydride or in the presence of potassium carbonate in acetonitrile, dimethylformamide or cyclic ketones, or with $R^{13}$COCl or

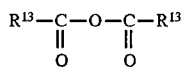

where $R^{13}$ is defined as in formula XI, where appropriate with catalysis by nitrogen bases such as pyridine, to give the corresponding phenol ethers or phenol esters.

24. The process of claim 23, further comprising the step of isolating the compound of the formula I which has been prepared by said process in free form or, if acidic or basic groups are present, converting it into physiologically tolerated crystalline salts.

25. A process for preparing the compound of the formula I as claimed in claim 1, said process comprising a) reacting a compound of the formula VII

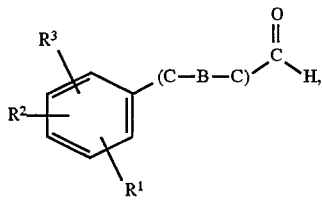

(VII)

where $R^1$, $R^2$ and $R^3$ are as defined in claim 1, and (C-B-C) is selected from a covalent bond, (—CH═CH—), (—CH$_2$—CH$_2$—CH$_2$), (—CH$_2$—CH$_2$) and (—CH$_2$—), with a compound of the formula VIII or a salt thereof,

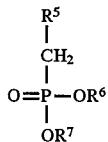

(VIII)

where $R^5$, $R^6$ and $R^7$, are defined as in claim 1, in the presence of tetrahydrofuran and titanium tetrachloride, or in the presence of tetrahydrofuran and an orthotitanic triester of the formula IX

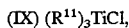 (IX) $(R^{11})_3$TiCl, where $R^{11}$ is —O—($C_1$-$C_6$)-alkyl, and (b) hydrogenating a compound of the formula I which has been prepared by process a), where $R^5$ is CN, in the presence of hydrogen and a Pd/C or Raney nickel catalyst.

26. The process of claim 25, further comprising the step ore isolating the compound of the formula I which has been prepared by step b) in free form or, if acidic or basic groups are present, converting it into physiologically tolerated crystalline salts.

27. The process of claim 25, further comprising reacting an amino compound which has been obtained by process b) with a ($C_1$-$C_3$)-alkylcarboxylic anhydride to the corresponding carboxamide.

28. A process for preparing the compound of the formula I as claimed in claim 1, said process comprising a) reacting a compound of the formula VII

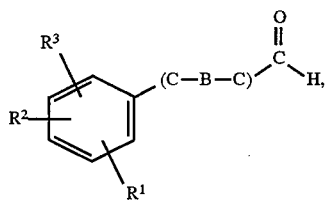

(VII)

where $R^1$, $R^2$ and $R^3$ are as defined in claim 1, and (C-B-C) is selected from a covalent bond, (—CH═CH—), (—CH$_2$—CH$_2$—CH$_2$), (—CH$_2$—CH$_2$) and (—CH$_2$—), with a compound of the formula VIII or a salt thereof,

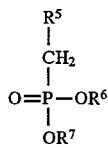

(VIII)

where $R^5$, $R^6$ and $R^7$ are defined as in claim 1, in the presence of tetrahydrofuran and titanium tetrachloride, or in the presence of tetrahydrofuran and an orthotitanic triester of the formula IX

 (IX) $(R^{11})_3$TiCl, where $R^{11}$ is —O—($C_1$-$C_6$)-alkyl, and b) converting a compound of the formula I which has been prepared by process a), where $R^5$ is —COOH, by esterification into the corresponding carboxylic ester, where the carboxylic acids are converted with oxalyl chloride into the carbonyl chloride, and the latter is reacted with $R^{10}$—OH.

29. A Pharmaceutical composition containing an effective amount of at least one compound of the formula (I)

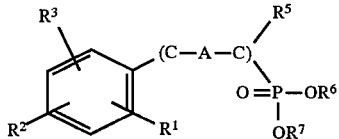

(I)

a physiologically tolerated salt thereof, or a stereoisomer thereof, where at least two of the radicals $R^1$, $R^2$ and $R^3$ are present and are, independently of one another, selected from 1) OH,
2) ($C_1$-$CH_{12}$)-alkoxy,
3) —O—($C_1$-$CH_{12}$)-alkyl-COOH,
4) —O—($C_1$-$C_{12}$)-alkyl-C(O)—O—($C_1$-$C_{12}$)-alkyl,
5) ($C_3$-$CH_{12}$)-cycloalkoxy,
6) ($C_3$-$C_6$)-alkenyloxy,
7) ($C_5$-$C_7$)-cycloalkyl-($C_1$-$C_3$)-alkoxy,
8) heteroaryl-($C_1$-$C_3$)-alkoxy, where the heteroatoms are selected from N, S and O,
9) heterocycloalkyl-($C_1$-$C_3$)-alkoxy where the heteroatoms are selected from N, S and O, the heterocycloalkyl radical is unsubstituted or substituted once to three times by ($C_1$-$C_3$)-alkyl, and the heterocycloalkyl group has five or six members,
10) phenyl-($C_1$-$C_3$)-alkoxy,
11) benzyloxy substituted once to three times by halomethyl or ($C_1$-$C_3$)-alkoxy,
12) phenoxy substituted once to three times by ($C_1$-$C_3$)-alkoxy, 13) two of the radicals $R^1$, $R^2$ or $R^3$ which are substituents on two directly adjacent carbon atoms of the aromatic ring together form a methylenedioxy or ethylenedioxy radical on the aromatic ring, 14) a radical of the formula II, III or IV

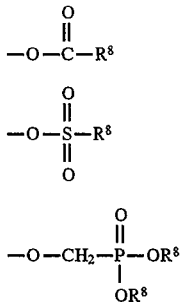

where $R^8$ is $(C_1-C_4)$-alkyl or hydrogen, 15) a group of the formula V

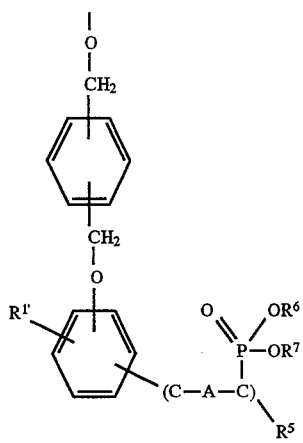

where

R' is defined as for $R^1$ from 1) to 12), and (C-A-C), , $R^5$, $R^6$ and $R^7$ are as defined below, or 16) $R^1$ and $R^7$ form a compound of the formula Ia

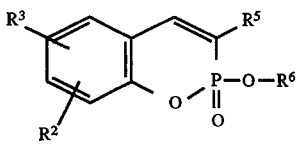

where $R^2$ and $R^3$ are as defined above and $R^5$ and $R^6$ are as defined below, and 17) $R^1$ and $R^5$ form a compound of the formula Ib

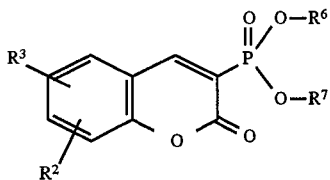

where $R^2$ and $R^3$ are as defined above and $R^6$ and $R^7$ are as defined below, and $R^5$ is selected from 1) CN,
2) $CH_2NHR^9$, where $R^9$ is hydrogen or —C(O)—$(C_1-C_3)$-alkyl, and
3) a radical of the formula VI

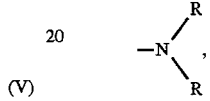

where $R^{10}$ is selected from 1) hydrogen,
2) $(C_1-C_6)$-alkyl, unsubstituted or substituted once to four times by a group selected from —COOH, —C(O)—O—$(C_1-C_3)$-alkyl and $$-N\begin{matrix}R\\R\end{matrix},$$

where R is hydrogen, $(C_1-C_3)$-alkyl or forms, together with the nitrogen atom to which it is bonded, a morpholine ring, and 3) trialkylsilyl, $R^6$ and $R^7$ are, independently of one another, 1) hydrogen or
2) $(C_1-C_6)$-alkyl, and (C-A-C) is selected from 1) (CH=CH—CH=CH—CH),
2) ($CH_2$—$CH_2$—$CH_2$—$CH_2$—CH),
3) ($CH_2$—$CH_2$—$CH_2$—CH),
4) ($CH_2$—$CH_2$—CH),
5) (—$CH_2$—CH) and
6) (—CH=C).

30. A method for the treatment of degenerative joint disorders, of rheumatic disorders accompanied by cartilage breakdown, of inflammations, septic shock, disorders accompanied by impaired leukocyte adhesion, or disorders caused by an elevated concentration of tumor necrosis factor alpha, said method comprising administering an effective amount of at least one compound of formula (I) as claimed in claim 1 to a human patient in recognized need of said treatment.

31. The method according to claim 30, wherein the rheumatic disorder accompanied by cartilage breakdown is rheumatoid arthritis, joint trauma, or chondrolysis resulting from prolonged immobilization.

32. The method according to claim 30, wherein the disorder caused by an elevated concentration of tumor necrosis factor alpha is cachexia or Crohn's disease.

* * * * *